(12) United States Patent
Che et al.

(10) Patent No.: US 10,038,153 B2
(45) Date of Patent: Jul. 31, 2018

(54) PLATINUM (II) EMITTERS FOR OLED APPLICATIONS

(71) Applicants: Chi Ming Che, Hong Kong (HK); Chi Fai Kui, Hong Kong (HK); Chi Chung Kwok, Hong Kong (HK)

(72) Inventors: Chi Ming Che, Hong Kong (HK); Chi Fai Kui, Hong Kong (HK); Chi Chung Kwok, Hong Kong (HK)

(73) Assignee: VERSITECH LIMITED, Hong Kong (HK)

( * ) Notice: Subject to any disclaimer, the term of this patent is extended or adjusted under 35 U.S.C. 154(b) by 819 days.

(21) Appl. No.: 14/243,950

(22) Filed: Apr. 3, 2014

(65) Prior Publication Data

US 2015/0287937 A1    Oct. 8, 2015

(51) Int. Cl.
*H01L 51/54*  (2006.01)
*C09K 11/06*  (2006.01)
*H01L 51/00*  (2006.01)
*C07F 15/00*  (2006.01)
*H01L 51/50*  (2006.01)

(52) U.S. Cl.
CPC ...... *H01L 51/0087* (2013.01); *C07F 15/0086* (2013.01); *C09K 11/06* (2013.01); *C09K 2211/1029* (2013.01); *C09K 2211/185* (2013.01); *H01L 51/5012* (2013.01); *H01L 51/5016* (2013.01)

(58) Field of Classification Search
None
See application file for complete search history.

(56) References Cited

U.S. PATENT DOCUMENTS

| | | | | |
|---|---|---|---|---|
| 9,306,178 B2* | 4/2016 | Che et al. | ............ | H01L 51/0087 |
| 2006/0060842 A1* | 3/2006 | Sano et al. | ............ | C09K 11/06 257/40 |
| 2006/0073359 A1* | 4/2006 | Ise et al. | ............ | C07F 15/0086 428/690 |
| 2006/0134461 A1* | 6/2006 | Huo et al. | ............ | C07F 15/0086 428/690 |
| 2006/0210831 A1* | 9/2006 | Sano et al. | ............ | C07F 15/0086 428/690 |
| 2012/0018711 A1* | 1/2012 | Che et al. | ............ | C07D 213/30 257/40 |
| 2015/0194615 A1* | 7/2015 | Lin et al. | ............ | C07F 15/0093 257/40 |

OTHER PUBLICATIONS

Yan et al., High-Efficiency Orange and Yellow Organic Light-Emitting Devices Using Platinum (II) Complexes Containing Extended Conjugated Cyclometalated Ligands as Dopants Materials, Applied Physics Letters 91, 2007, pp. 063508-1-063508-3.
Zhao et al., A3-Dimensional Spiro-Functionalized Platinum (II) Complex to Supress Intermolecular and Pt . . . Pt Supramolecular Interactions for a High-Performance Electrophosphorescent Device, Chem. Commun., 2012, 48, 3854-3856.
Kui, et al, Robust Phosphorescent Platinum (II) Complexes with Tetradentate ONCN Ligands: High Efficiency OLEDs with Excellent Efficiency Stability, Chem, Commun., 2013, 49, 1497-1499.
Che et al, Photophysical Properties and OLED Applications of Phosphorescent Platinum (II) Schiff Based Complexes, Chem., Eur. J. 2010,16, 233-247.
Vezzu et al., Highly Luminescent Tetradentate Bis-Cyclometalated Platinum Complexes: Design, Synthesis, Structure, Photophysics, and Electroluminescene Application, Inorg. Chem. 2010, 49, 5107-5119.

* cited by examiner

Primary Examiner — Marie R. Yamnitzky
(74) Attorney, Agent, or Firm — Amin, Turocy & Watson, LLP

(57) ABSTRACT

Described herein are novel platinum(II) emitters. These materials show high emission quantum efficiency, a low self-quenching constant, and are stable in thermal deposition processes. Organic light-emitting diodes (OLEDs) fabricated from these materials can have pure green emission, high efficiency and low efficiency roll-off. The OLEDs can have a chemical structure of:

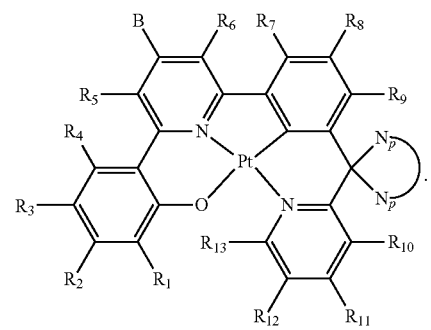

18 Claims, 6 Drawing Sheets

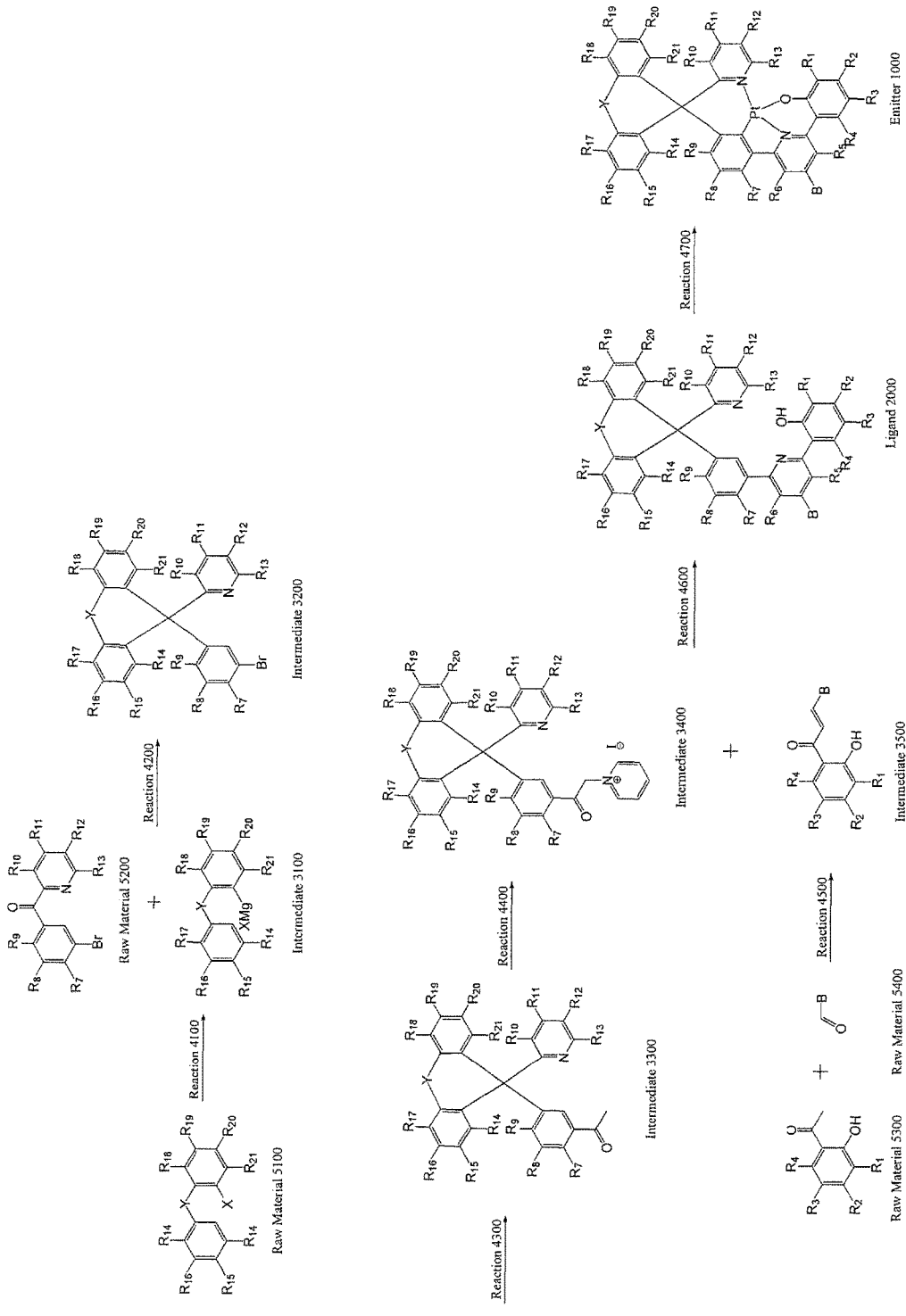
Figure 1: Synthetic Scheme of the Emitters.

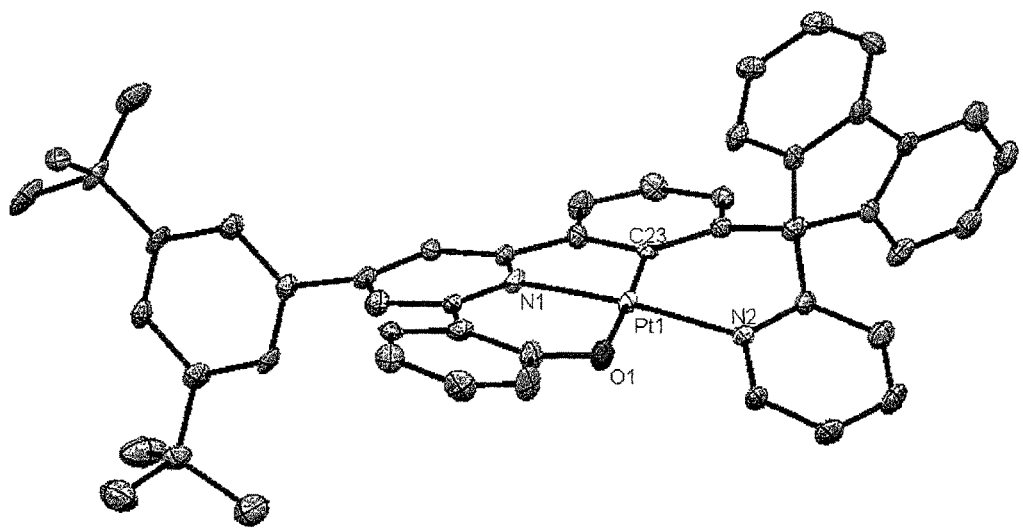
Figure 2: X-Ray structure of Emitter 1002
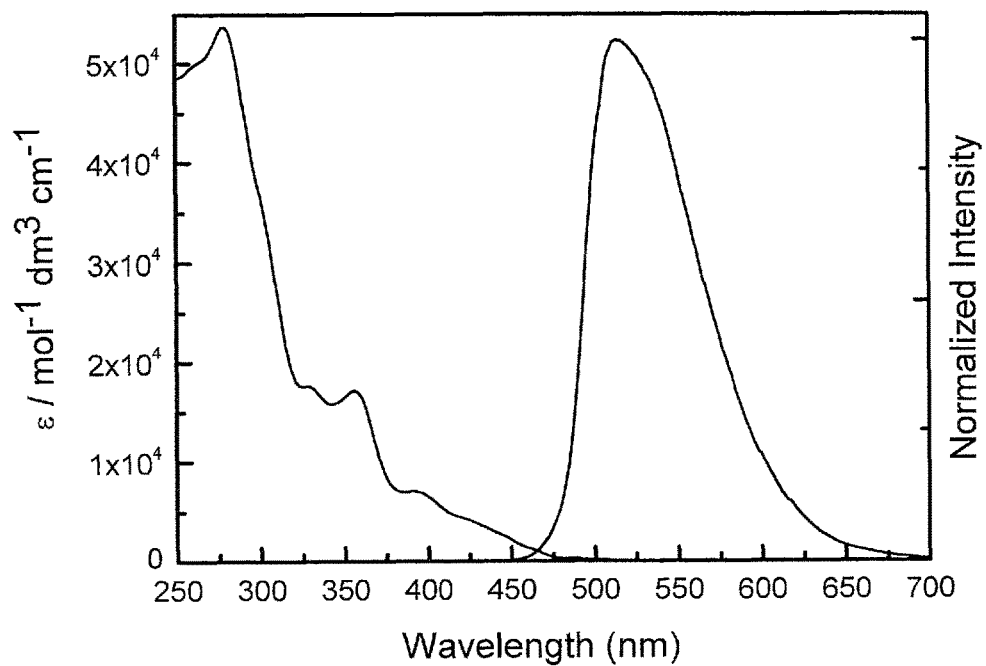
Figure 3: UV-Vis absorption and emission spectra of Emitter 1002

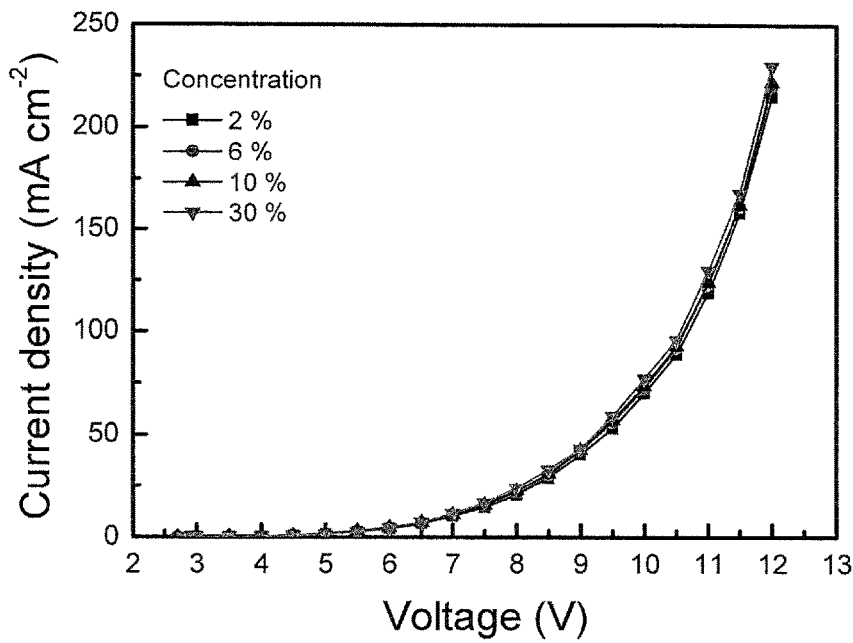
Figure 4: Current density – voltage graphs of the OLEDs fabricated from Emitter 1002.
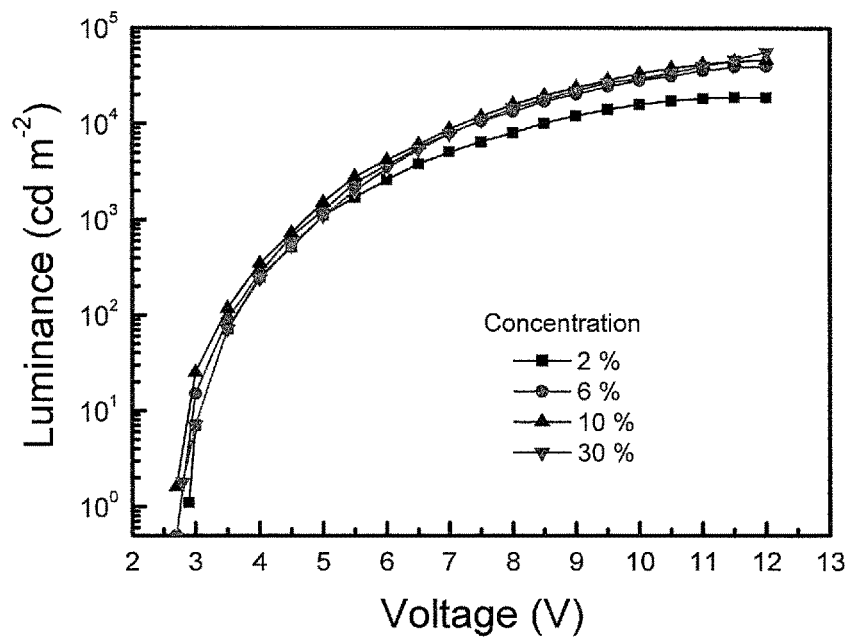
Figure 5: Luminance – voltage graphs of the OLEDs fabricated from Emitter 1002.

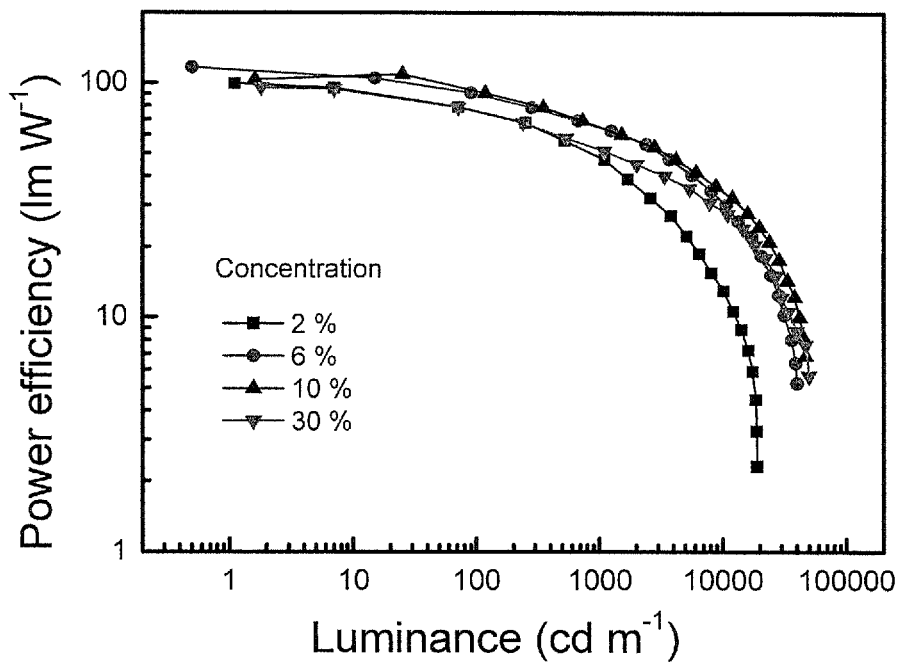
Figure 6: Power efficiency-luminance graphs of the OLEDs fabricated from Emitter 1002.
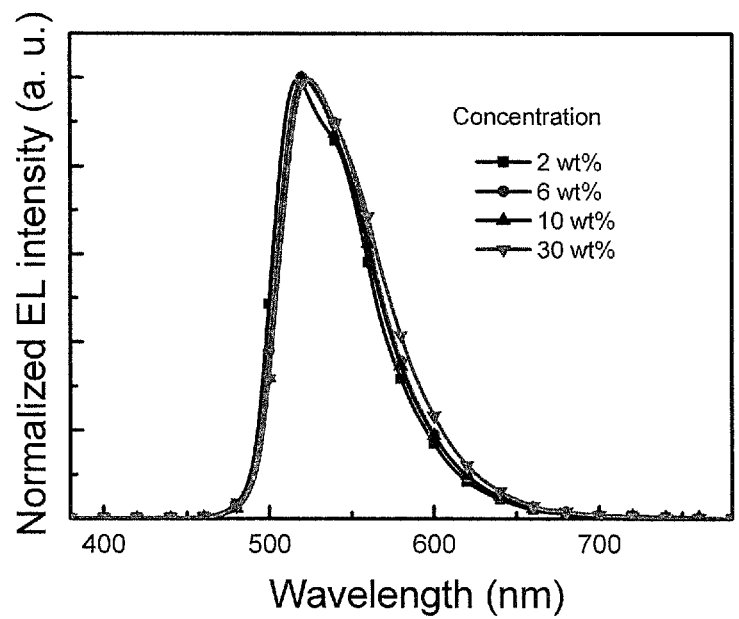
Figure 7: EL spectra of the OLEDs fabricated from Emitter 1002.

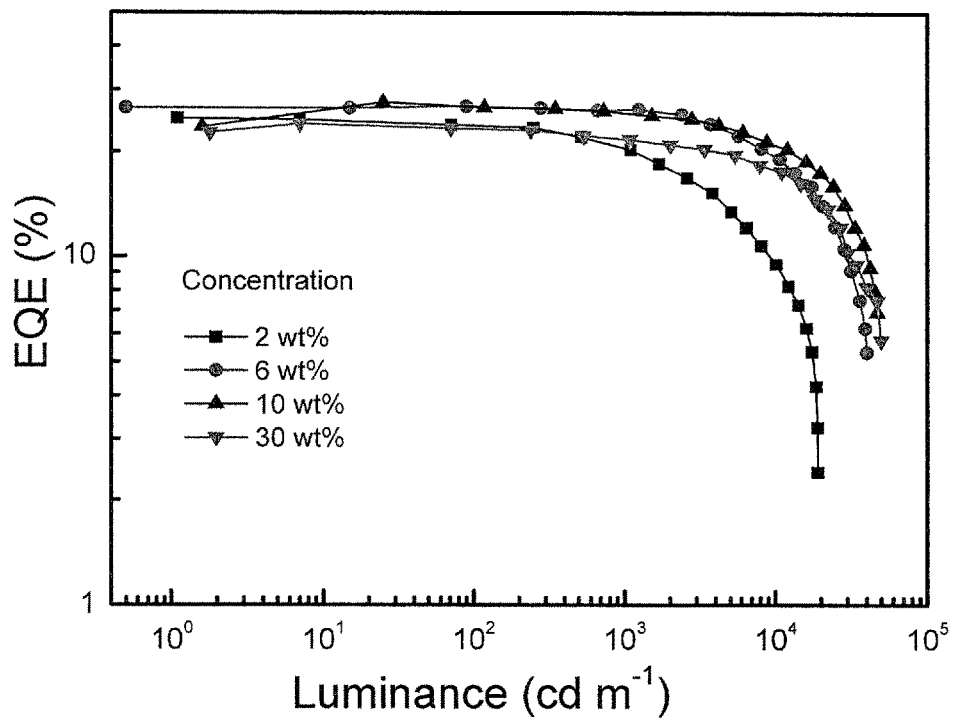
Figure 8: Efficiency cures of the OLEDs fabricated from Emitter 1002.
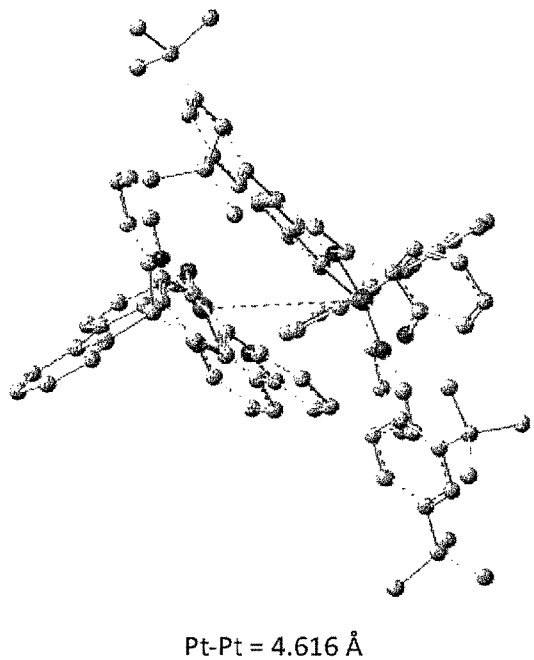
Pt-Pt = 4.616 Å
Figure 9: The optimized geometries of Emitter 1002

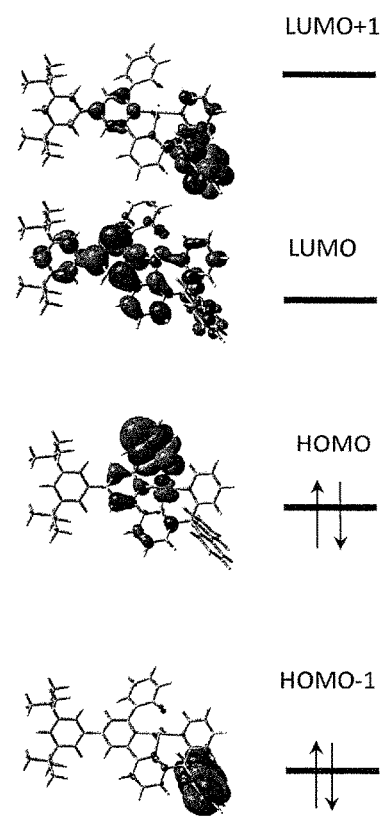
Figure 10: Frontier MO diagram of Emitter 1002
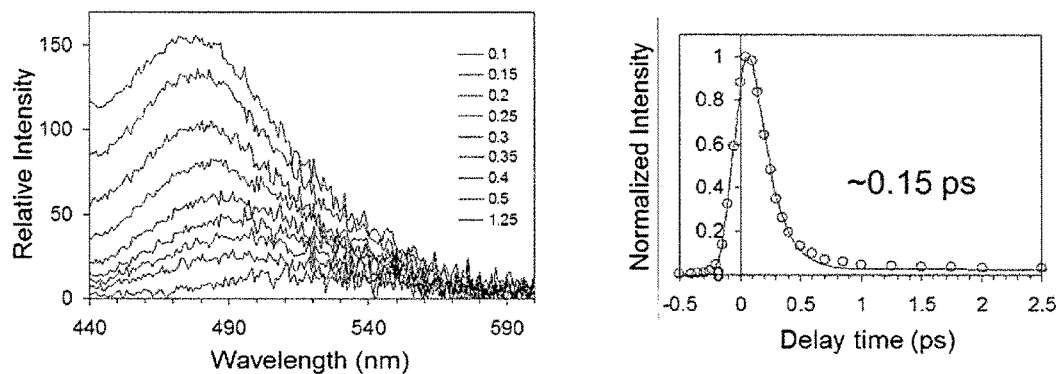
Figure 11: Time-resolved fluorescent of Emitter 1002 in $CH_2Cl_2$ with excitation at 350 nm.

PLATINUM (II) EMITTERS FOR OLED APPLICATIONS

TECHNICAL FIELD

Described herein are class platinum(II) emitters their preparation and applications in organic light-emitting diode (OLED).

BACKGROUND

Even platinum is better than iridium in natural abundance and cost, nowadays, only iridium(III) emitters are used OLED display panels. Many remaining issues have to be solved before platinum(II) emitters can be used in OLED display panel production. Efficiency roll-off is one of the most important issues encounter by platinum(II) emitters. It is because platinum emitters adopt a square planar geometry and the platinum centers tends to come together, platinum (II) emitters usually have very high self-quenching constants (in the order of $10^8$ $dm^3$ $mol^{-1}$ $s^{-1}$ or more). Together with the long emission lifetime (near or longer than 10 μs), the devices fabricate from platinum(II) emitters usually have severe triple-triplet annihilation leading to serious efficiency roll-off.

Limited by the low emission quantum efficiency, OLEDs fabricated from platinum(II) emitter have shown related low efficiency. In the past decade, due to the improvement in emission quantum efficiency, the maximum device efficiency of 51.8 cd/A has been achieved by platinum(II) emitters [Appl. Phys. Lett. 91, 063508 (2007)]. However, the efficiencies of these device drops to less than 50% of the maximum values when the brightness increased to acceptable operation brightness say 1,000 $cdm^{-2}$. This is not good for OLED applications.

Besides serious efficiency roll-off, OLEDs fabricated from emitters which tend to come together (in the other words: tends to self-aggregate/have high self-quenching constant) always have narrow doping window (devices with high efficiency and good color purity can only be obtained in a very narrow doping concentration range such as 1 wt. %-5 wt. %). As the fabrication systems in industry are much large than those in research institutes, making devices within such narrow doping window is not an easy task. As a result, platinum(II) materials are not yet been used in industry.

Some efforts have been made to deal with this issue. Bulky groups such as tert-butyl group(s) and non-planar phenyl group have been added to the emitters. However, they are not successful. In 2010, Che added tert-butyl group(s) in red-emitting platinum(II) material. [Chem. Eur. J. 2010, 16, 233-247]. However, close intermolecular stacking π-π interactions were still observed in the X-Ray crystal structure which means the problem cannot be resolved.

In the same year, Huo report a class of platinum(II) materials containing a non-planar phenyl ring, however excimer emission appears in doping concentration more than 4 wt. % and severe triplet-triplet annihilation was observed even in a device with a mix host, which means this approach cannot solve the problem [Inorg. Chem. 2010, 49, 5107-5119].

In 2013, Xie prepared new emitters containing two non-planar spiro-structures. [Chem. Commun. 2012, 48, 3854-3856] However, the devices fabricated by this emitter show serious efficiency roll-off of >50% which indicates adding non-planar group(s) may able to reduce roll-off.

In the same year, Che combined the two approaches and using a new, robust (O^N^C^N) ligand system to prepare new platinum(II) materials. In this approach, one of the emitters shows a wide doping window and slow efficiency roll-off [Chem. Commun. 2013, 49, 1497-1499]. However, the quenching constants of these materials are still high (minimum value: $8.82 \times 10^{-7}$ $dm^3$ $mol^{-1}$ $s^{-1}$) which made the maximum efficiency of the device only achieve 66.7 cd/A, whereas even the emission quantum efficiency of the device is 90%. Close or more than 100 cd/A should be obtained with this emission quantum efficiency if the quenching effect is resolved.

SUMMARY

In this invention, we design platinum(II) emitters with a new ligand core which have high emission quantum efficiencies, small self-quenching constants. They are ready to be used in industry.

The invention relates to novel platinum(II) emitters having the chemical structure of Structure I. Also provided are methods of preparing the platinum(II)-based materials, and their applications in organic light-emitting diode (OLED).

In one embodiment, the platinum(II)-based compounds of Structure I are shown as follows:

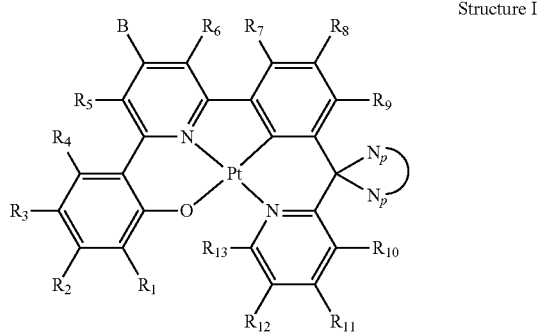

Structure I wherein $R_1$-$R_{13}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each pair of adjacent R groups of $R_1$-$R_{13}$ can independently form 5-8 member ring(s) with 2 or 4 carbon atoms in the phenyl ring(s) showed in Structure I; B and

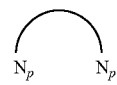

are self-quenching reduction groups.

The invention also provides devices fabricated from the platinum(II) emitters of Structure I. Advantageously, the devices of the invention exhibit at least one of and often both of high efficiency and low roll-off. Pure green emission can also be obtained in this material system.

BRIEF DESCRIPTION OF THE DRAWINGS

FIG. 1: Synthetic Scheme of the Emitters.
FIG. 2: X-Ray structure of Emitter 1002.

FIG. 3: UV-Vis absorption and emission spectra of Emitter 1002.

FIG. 4: Current density-voltage graphs of the OLEDs fabricated from Emitter 1002.

FIG. 5: Luminance-voltage graphs of the OLEDs fabricated from Emitter 1002.

FIG. 6: Power efficiency-luminance graphs of the OLEDs fabricated from Emitter 1002.

FIG. 7: EL spectra of the OLEDs fabricated from Emitter 1002.

FIG. 8: Efficiency cures of the OLEDs fabricated from Emitter 1002.

FIG. 9: The optimized geometries of Emitter 1002

FIG. 10: Frontier MO diagram of Emitter 1002

FIG. 11: Time-resolved fluorescent of Emitter 1002 in CH2Cl2 with excitation at 350 nm.

DETAILED DESCRIPTION

Definitions

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of an amino group include —NR'R" wherein each of R' and R" is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. Examples of alkyl groups include, but are not limited to, methyl, ethyl, n-propyl, isopropyl, n-butyl, t-butyl, n-heptyl, n-hexyl, n-octyl, and n-decyl.

"Alkylamino" means a radical —NHR or —NR$_2$ where each R is independently an alkyl group. Representative examples of alkylamino groups include, but are not limited to, methylamino, (1-methylethyl)amino, methylamino, dimethylamino, methylethylamino, and di(1-methyethyl)amino.

The term "hydroxyalkyl" means an alkyl radical as defined herein, substituted with one or more, preferably one, two or three hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl, and 1-(hydroxymethyl)2-hydroxyethyl.

The term "alkoxy," as used herein, refers the radical —OR$_x$. Exemplary alkoxy groups include, but are not limited to, methoxy, ethoxy, and propoxy.

"Aromatic" or "aromatic group" refers to aryl or heteroaryl.

"Aryl" refers to optionally substituted carbocyclic aromatic groups. In some embodiments, the aryl group includes phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Styryl" refers to a univalent radical C$_6$H$_5$—CH=CH— derived from styrene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl; heteroaryl; hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —CO$_2$CH$_3$; —CONH$_2$; —OCH$_2$CONH$_2$; —NH$_2$; —SO$_2$NH$_2$; —OCHF$_2$; —CF$_3$; —OCF$_3$; —NH(alkyl); —N(alkyl)$_2$; —NH(aryl); —N(alkyl)(aryl); —N(aryl)$_2$; —CHO; —CO(alkyl); —CO (aryl); —CO$_2$(alkyl); and —CO$_2$(aryl); and such moieties can also be optionally substituted by a fused-ring structure or bridge, for example —OCH$_2$O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

In one aspect, the invention provides platinum(II) emitters. In one embodiment, an organometallic emitter represented by Structure I is provided. The platinum center in Structure I is in +2 oxidation state and has a square planar geometry. The coordination sites of the platinum center are occupied by a tetradentate ligand. The tetradentate ligand featuring with 6-5-6 fused membered rings coordinates to the platinum center through a metal-oxygen bond, a nitrogen donor bond, a metal-carbon bond and a nitrogen donor bond in a sequence of O, N, C, N (OˆNˆC*N ligand; i.e., 4 connecting covalent bonds (either single or double) between OˆN, 3 connecting covalent bonds (either single or double)

between N^C, 4 connecting covalent bonds (either single or double) between C*N). The metal-oxygen bond is a bond between deprotonated phenol or substituted phenol and platinum, the nitrogen donors are from pyridine and/or isoquinoline groups, and the metal-carbon bond is formed by benzene or substituted benzene and platinum. There must a one carbon atom between the aromatic systems of C*N of the O^N^C*N system. Two different self-quenching reduction groups are attached in specific position in a specific fashion.

Platinum(II) Emitters

In one embodiment, the platinum(II) emitters have the chemical structures of Structure I:

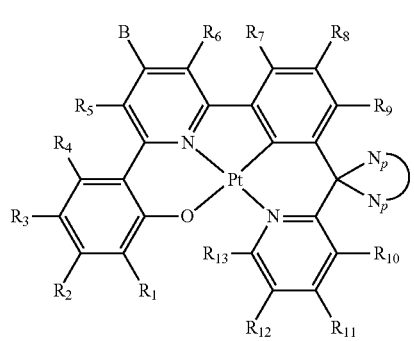

Structure I wherein $R_1$-$R_{13}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each pair of adjacent R groups of $R_1$-$R_{13}$ can independently form 5-8 member ring(s) with 2 or 4 carbon atoms in the phenyl ring(s) showed in Structure I; B and

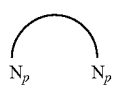

are self-quenching reduction groups.

In one embodiment, B is connected to the emitter in the position depicted in Structure I through a single covalent bond.

In one embodiment, is connect to the emitter in the position depicted in Structure I through two single covalent bond to the carbon atom between the C*N of the O^N^C*N system through a spiro-linkage.

In one embodiment, $R_1$-$R_{13}$ is independently hydrogen, halogen, hydroxyl, an unsubstituted alkyl containing from 1 to 10 carbon atoms, a substituted alkyl containing from 1 to 20 carbon atoms, cycloalkyl containing from 4 to 20 carbon atoms, an unsubstituted aryl containing from 6 to 20 carbon atoms, a substituted aryl containing from 6 to 20 carbon atoms, acyl containing from 1 to 20 carbon atoms, alkoxy containing from 1 to 20 carbon atoms, acyloxy containing from 1 to 20 carbon atoms, amino, nitro, acylamino containing from 1 to 20 carbon atoms, aralkyl containing from 1 to 20 carbon atoms, cyano, carboxyl containing from 1 to 20 carbon atoms, thio, styryl, aminocarbonyl containing from 1 to 20 carbon atoms, carbamoyl containing from 1 to 20 carbon atoms, aryloxycarbonyl containing from 1 to 20 carbon atoms, phenoxycarbonyl containing from 1 to 20 carbon atoms, or an alkoxycarbonyl group containing from 1 to 20 carbon atoms.

B is typically a hydrocarbon group containing 1 to 24 carbon atoms. For example, B can be a substituted aryl group. In one embodiment, B contains at least one t-butyl group. In another embodiment, B is:

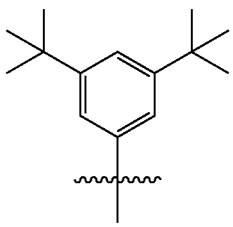 [SMILES: *c1cc(C(C)(C)C)cc(C(C)(C)C)c1]

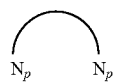

is typically a hydrocarbon group containing 2 to 40 carbon atoms.

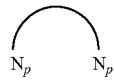

can be a substituted aryl group. In one embodiment,

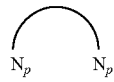

contains at least one benzyl group. In another embodiment, wherein

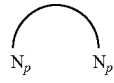

is:

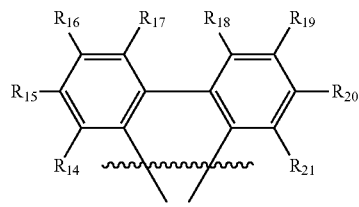

wherein $R_{14}$-$R_{21}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each pair of adjacent R groups of $R_{14}$-$R_{21}$ can independently form 5-8 member ring(s) with 2 or 4 carbon atoms in the phenyl ring(s).

In one embodiment, wherein

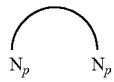

is:

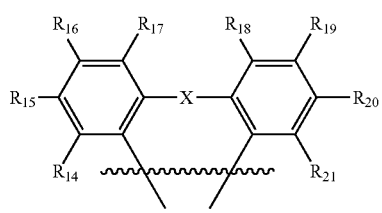

wherein X is selected from C, N, O, S, P or Si; $R_{14}$-$R_{21}$ are independently hydrogen, halogen, a hydroxy, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each pair of adjacent R groups of $R_{14}$-$R_{21}$ can independently form 5-8 member ring(s) with 2 or 4 carbon atoms in the phenyl ring(s).

Certain specific, non-limiting examples for the platinum (II) emitters with structure I are shown as follows:

Emitter 1001

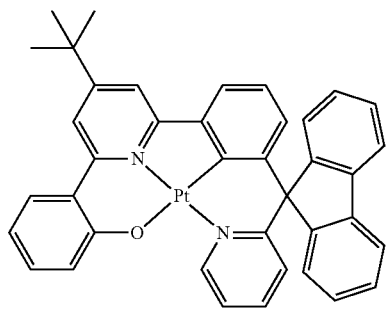

Emitter 1002

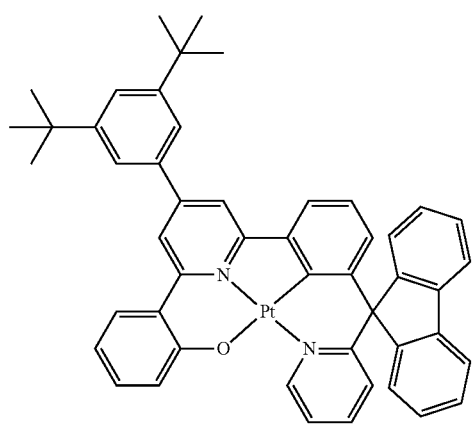

Emitter 1003

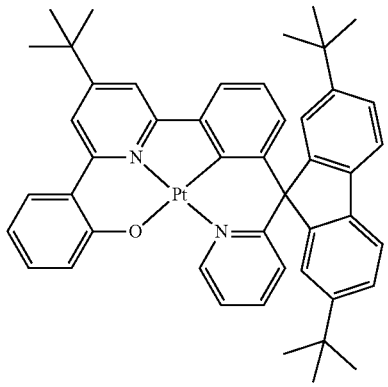

Emitter 1004

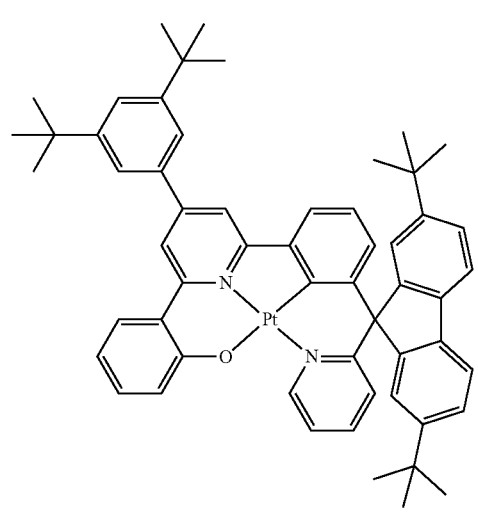

Emitter 1005

Emitter 1006

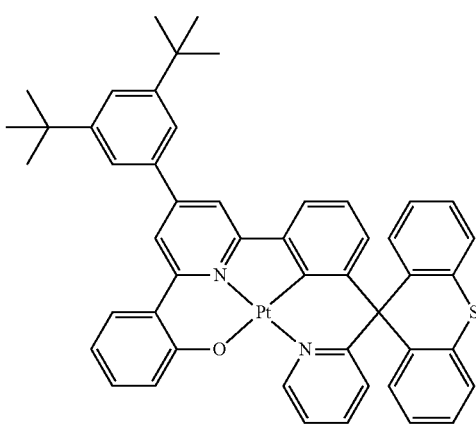

Emitter 1007
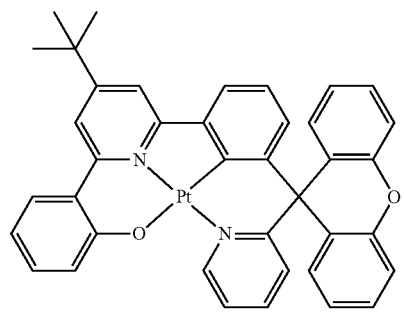
Emitter 1008
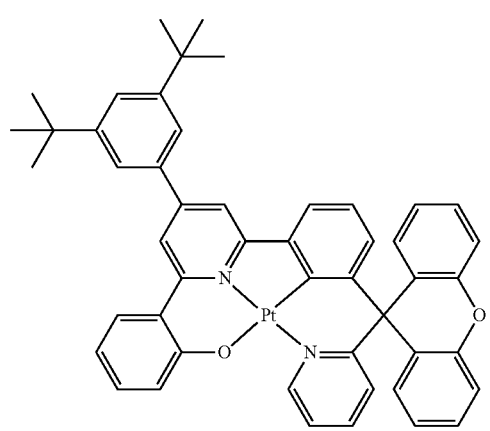
Emitter 1009
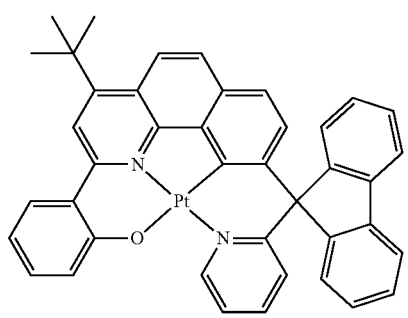
Emitter 1010
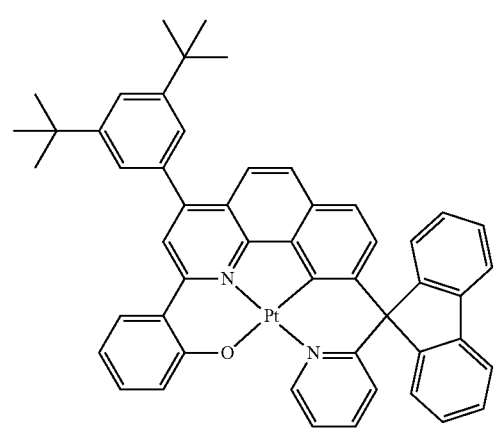
Emitter 1011
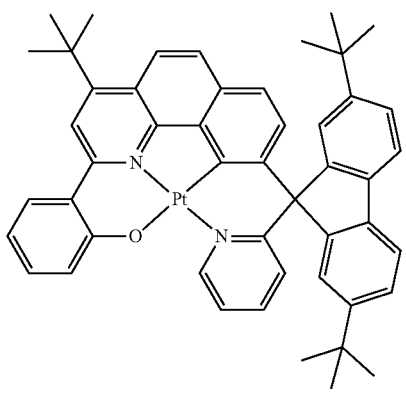
Emitter 1012
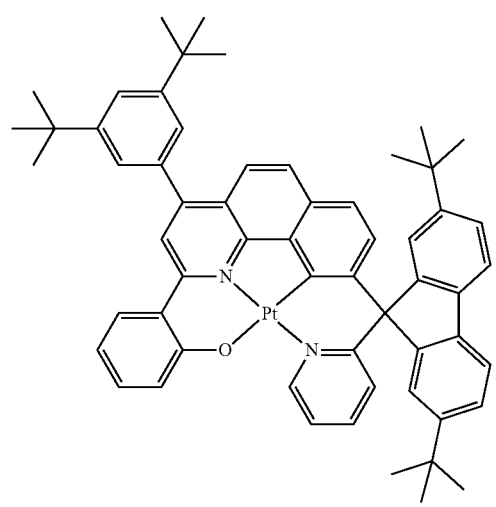
Emitter 1013
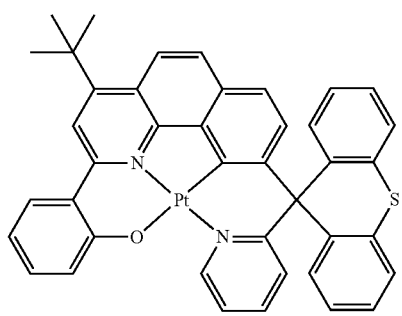

Emitter 1014
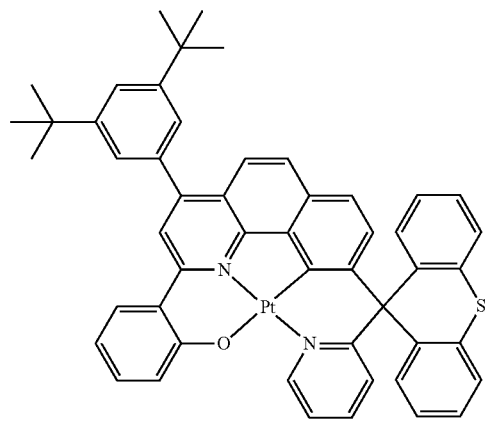
Emitter 1015
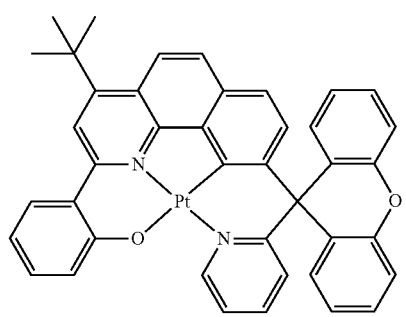
Emitter 1016
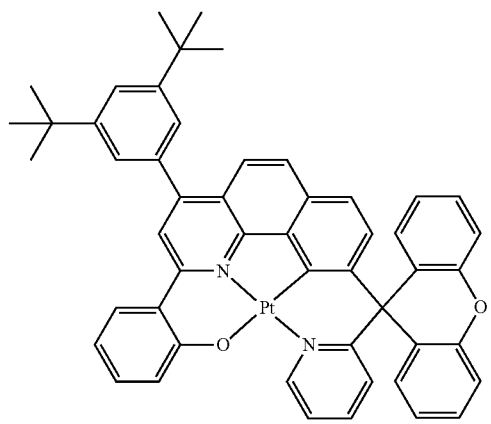
Emitter 1017
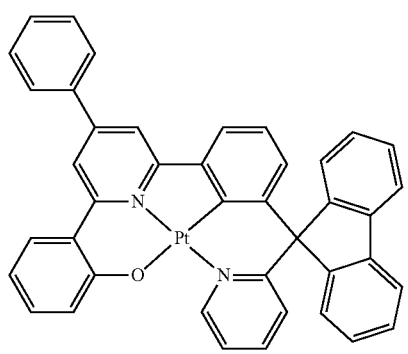
Emitter 1018
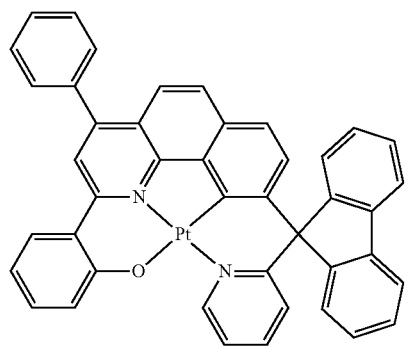
Emitter 1019
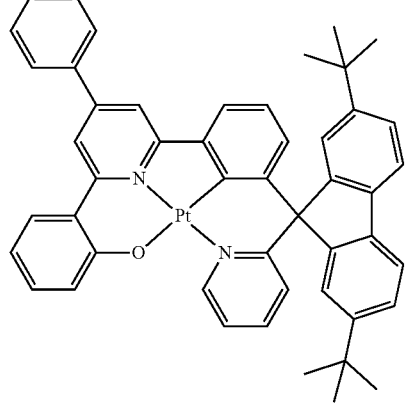
Emitter 1020
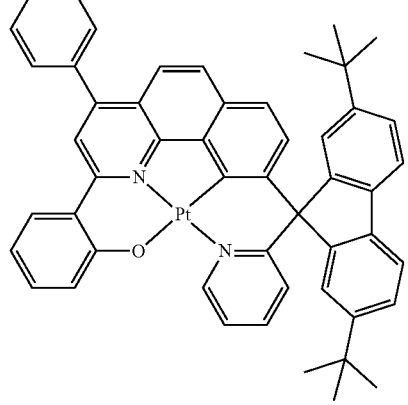
Emitter 1021
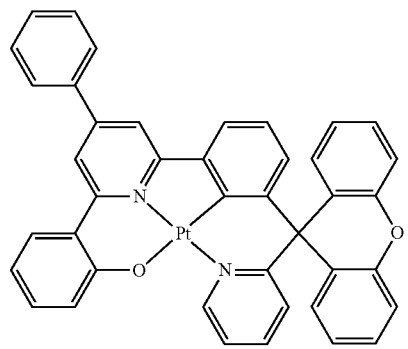

Emitter 1022
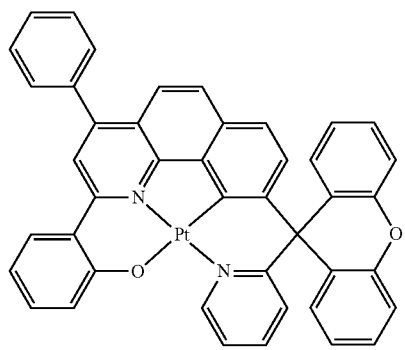
Emitter 1023
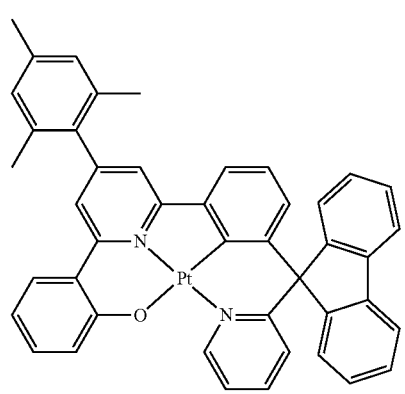
Emitter 1024
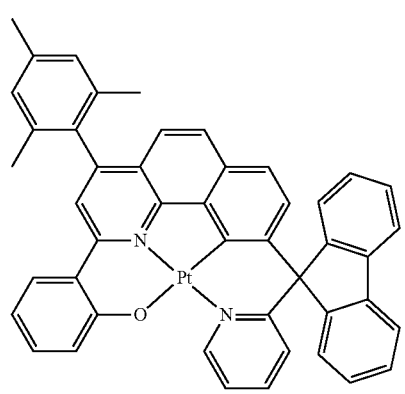
Emitter 1025
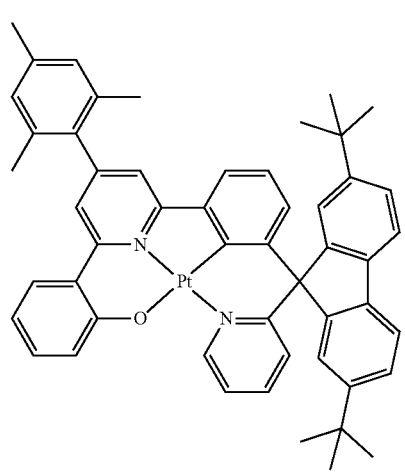
Emitter 1026
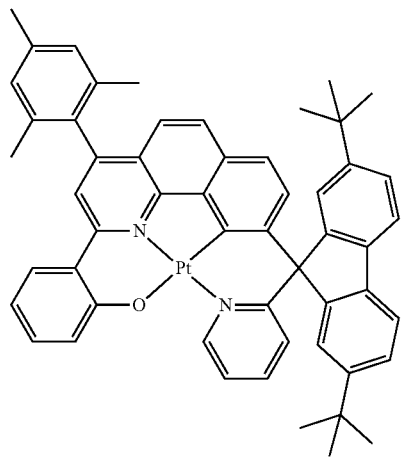
Emitter 1027
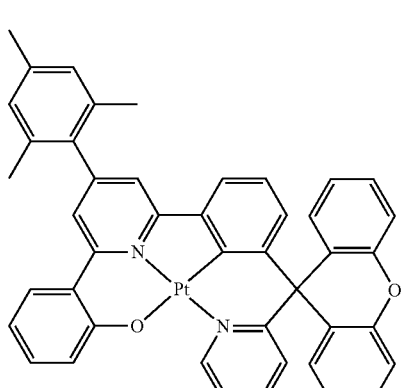
Emitter 1028
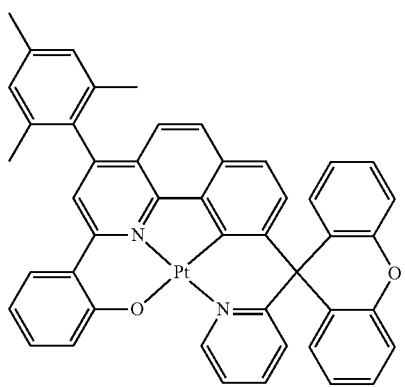
Preparation of Platinum(II) Emitter
In one embodiment, the platinum(II) emitter with chemical structure of Structure I can be prepared from a tetradentate ligand with a chemical structure of Structure II:

Structure II

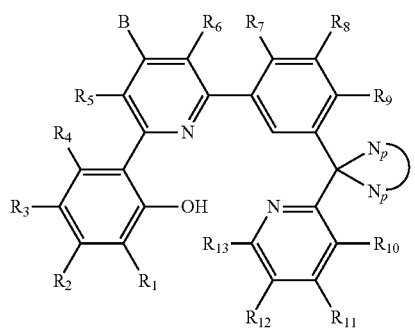

wherein $R_1$-$R_{13}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each pair of adjacent R groups of $R_1$-$R_{13}$ can independently form 5-8 member ring(s) with 2 or 4 carbon atoms in the phenyl ring(s) showed in Structure I; B and

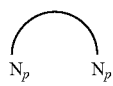

are self-quenching reduction groups.

Certain specific non-limiting examples of the tetradentate ligand with Structure II are shown below:

Ligand 2001

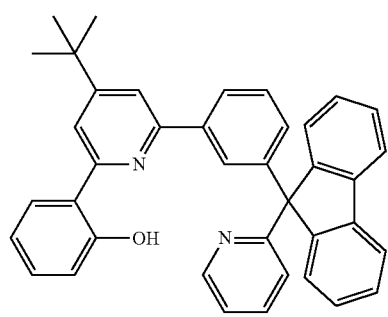

Ligand 2002

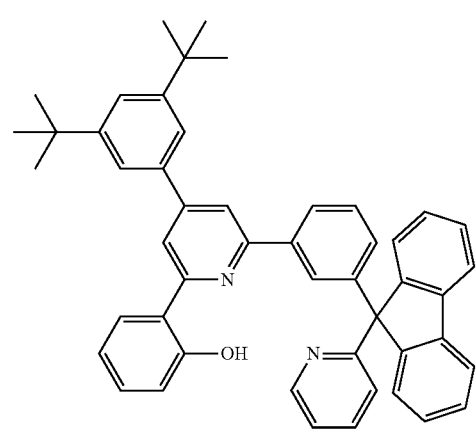

Ligand 2003

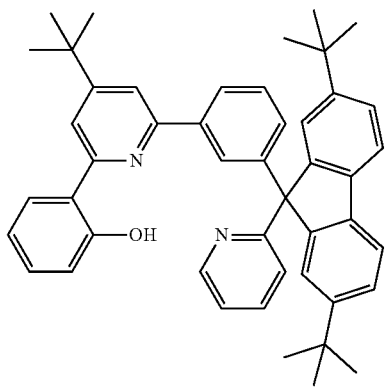

Ligand 2004

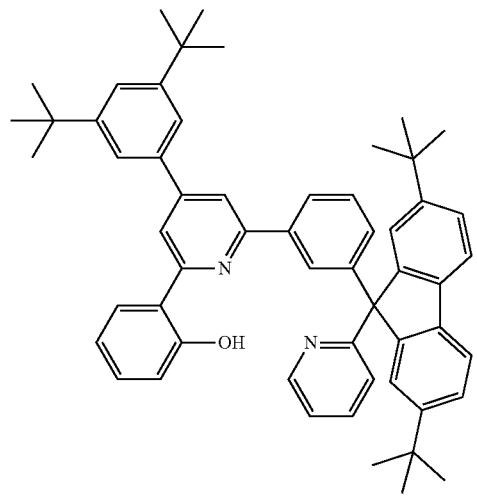

Ligand 2005

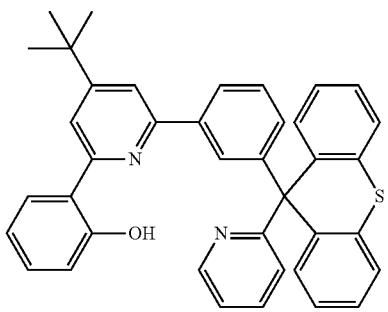

Ligand 2006

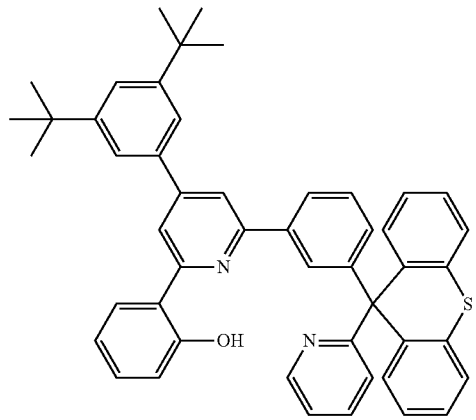

Ligand 2007
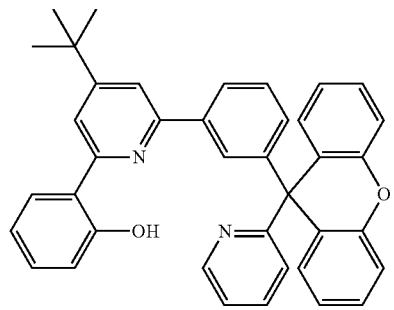
Ligand 2008
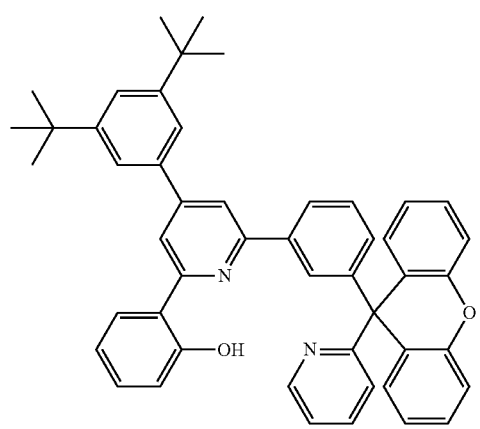
Ligand 2009
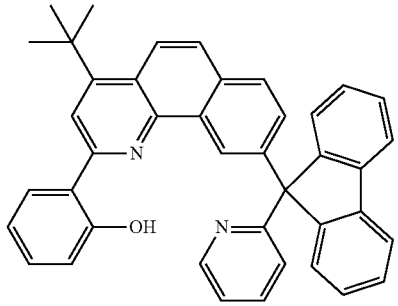
Ligand 2010
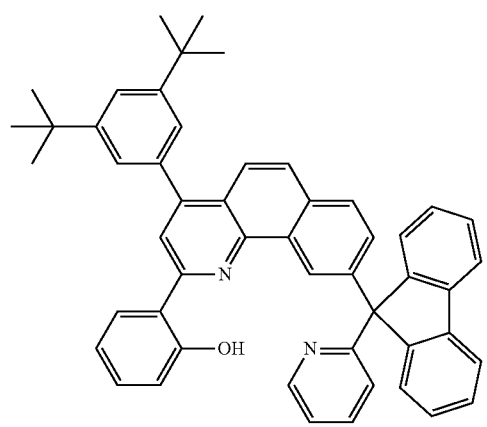
Ligand 2011
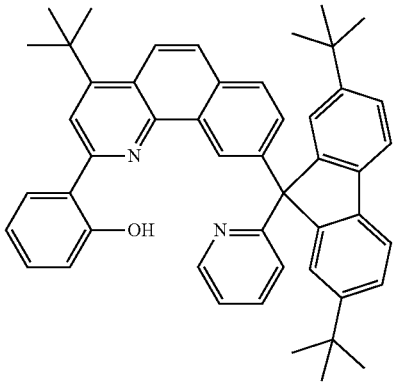
Ligand 2012
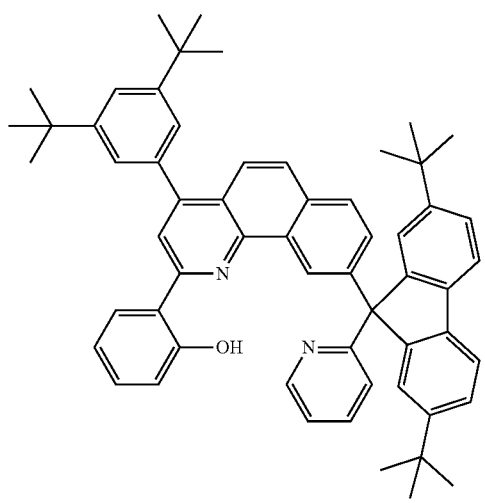
Ligand 2013
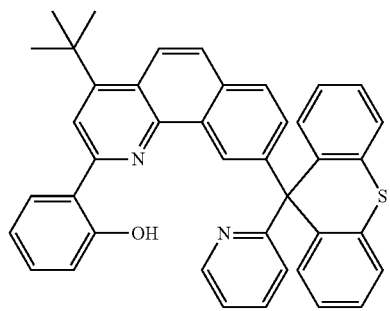
Ligand 2014
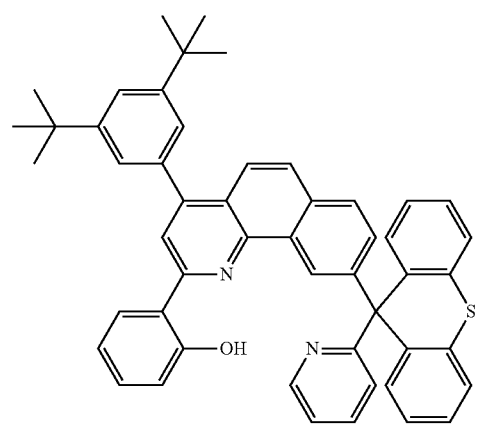

Ligand 2015
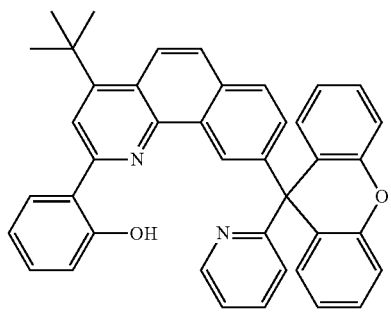
Ligand 2016
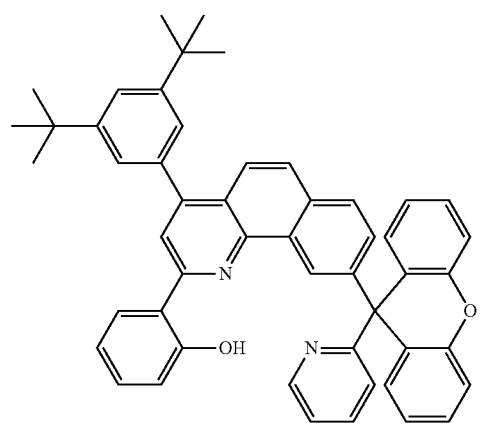
Ligand 2017
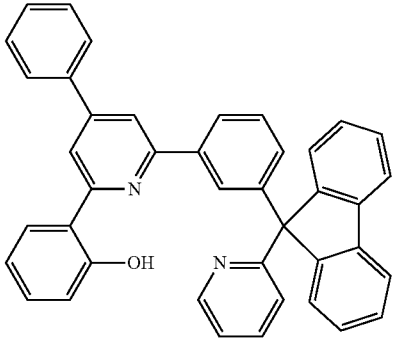
Ligand 2018
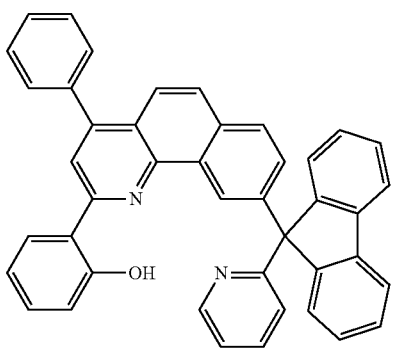
Ligand 2019
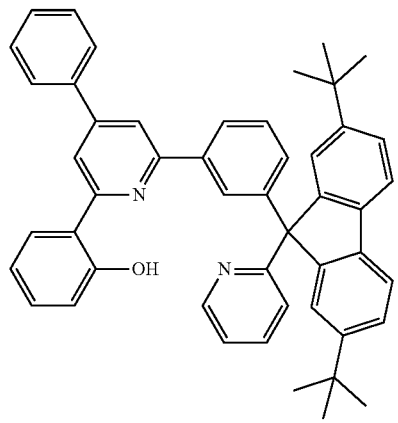
Ligand 2020
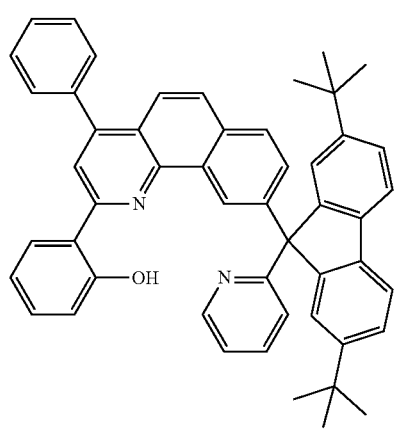
Ligand 2021
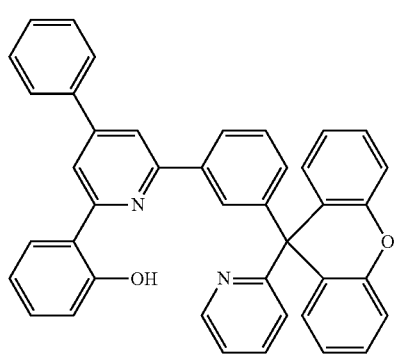
Ligand 2022
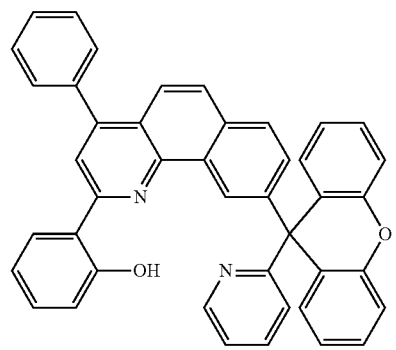

Ligand 2023

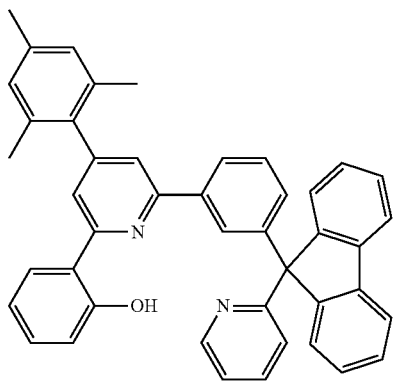

Ligand 2024

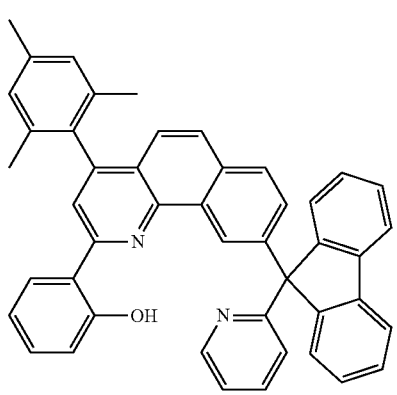

Ligand 2025

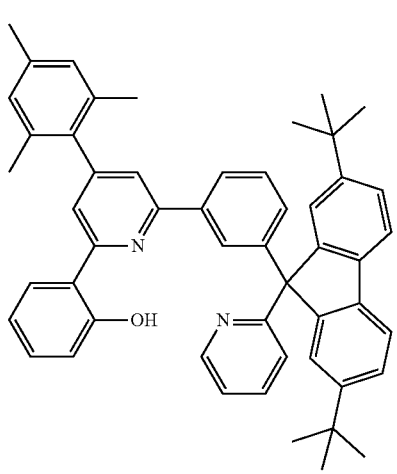

Ligand 2026

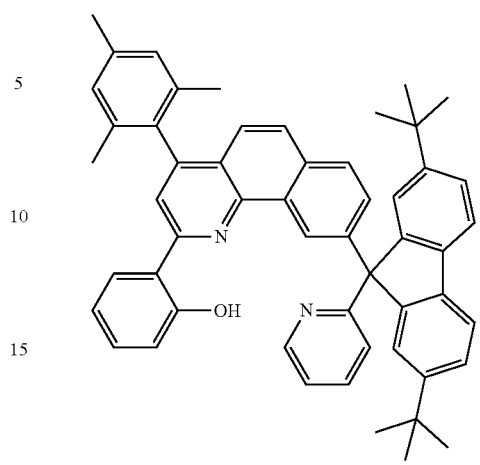

Ligand 2027

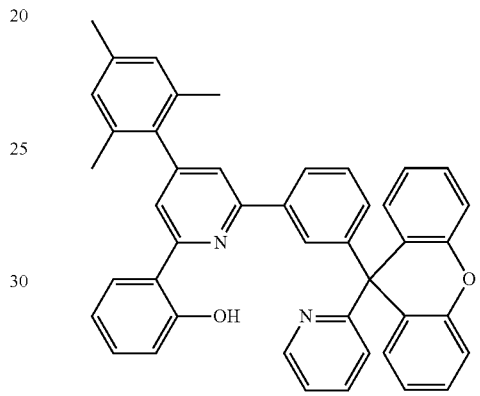

Ligand 2028

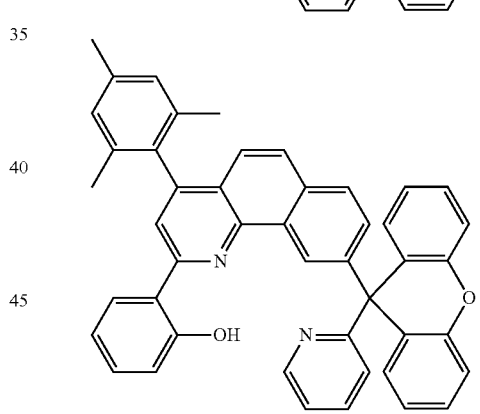

In one embodiment, the tetradentate ligand with Structure II can be prepared by a series of reactions depicted in FIG. 1:

According to FIG. 1, Raw Material 5100 is transformed to Intermediate 3100 by Reaction 4100 and then reacts with Raw Material 5200 to get Intermediate 3200 by Reaction 4200. Intermediate 3300 is then produced by Intermediate 3200 by Reaction 4300. Through Reaction 4400, Intermediate 3300 is converted to Intermediate 3400. On the other hand, Intermediate 3500 is prepared reacting Raw Material 5300 and Raw Materials 5400 through Reaction 4500. Afterward, Intermediate 3400 reacts with Intermediate 3500 to form the Ligand 2000. Finally, the Emitter 1000 is prepared from the Ligand by Reaction 4700.

In one embodiment, Reaction 4100 is a Grignard Reagent preparation reaction.

In one embodiment, Reaction 4200 is a Grignard Reaction followed by dehydration reaction using concentrated $H_2SO_4$.

In one embodiment, Reaction 4300 is a Stille coupling reaction.

In one embodiment, Reaction 4400 is reacting the Intermediate with iodine using pyridine as solvent.

In one embodiment, Reaction 4500 is a condensation reaction.

In one embodiment, Reaction 4600 is performed in the presence of excess ammonium acetate and a solvent under a reflux condition.

In one embodiment, Reaction 4700 is reacting a ligand with a platinum(II) salt in the presence of solven(s). In one embodiment, the platinum(II) salt is potassium tetrachloroplatinate. In another embodiment, the solvents are glacial acetic acid and chloroform.

Physical Properties Related to Industrial Applications

There are many standards to be meet before an emitter can be used in industry, here are the standards that the emitters in current invention met.

1. The emitters must have high emission quantum efficiency. In one embodiment, the emission quantum efficiency of the platinum(II) emitter is higher than 50%. The 6-5-6 fused ring ONC*N core is an important configuration to obtain high emission quantum efficiency. For example the emission quantum efficiency of the materials with ONN*C core are decreased significantly ($\phi$<1%).

2. The emitters must have pure red, green or blue emission for display panel application. In one embodiment, the platinum(II) emitters show pure green emission with solution emission $\lambda_{max}$ of 517±3 nm and CIE coordinates of (0.31±0.02; 0.63±0.02). This can only be achieved by using a carbon atom at $C^a$ location:

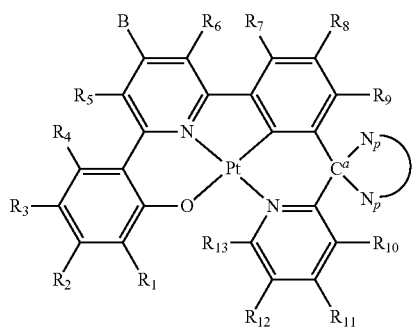

Replacing $C^a$ by other atom such as nitrogen leading to red-shift in emission, no green emission can be obtained in those materials which made them not suitable for display panel application.

3. The emitter must have a short emission lifetime, say less than 10 μs, to reduce triple-triplet annihilation. In one embodiment, the emission lifetime of the emitter is 5.1 μs or less. This cannot be achieved by a system of:

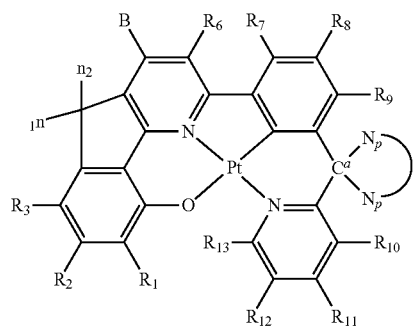

The emitters in this system show long emission lifetime of greater than 10 μs.

4. The emitter mush have high decomposition and without remainder in crucible after thermal deposition. In one embodiment, the deposition temperature determined by TGA is larger than 400° C. and does not have any remainder in crucible after thermal deposition. The 6-5-6 fused ring ONC*N core with a carbon atom at the $C^a$ position is an important configuration to obtain this property. For example, remainders usually appear in the materials with a nitrogen atom at the $C^a$ position.

5. The emitters much have self-quenching constant. In one embodiment, the self-quenching constant for the emitter are in the order of $10^7$ $dm^3$ $mol^{-1}$ $s^{-1}$ or lower, including, but not limited to, lower than in the order of $7\times10^6$, $5\times10^6$, $3\times10^6$, $10^6$, $7\times10^5$, $5\times10^5$, $3\times10^5$, or $10^5$ $dm^3$ $mol^{-1}$ $s^{-1}$. This can only achieved by incorporating both B and

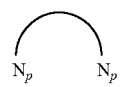

groups in the emitter.

6. The emitters must show high efficiency in single host device without out-coupling technique. In one embodiment, the device fabricated from the emitter in current invention shows maximum efficiency greater than 20% (external quantum efficiency).

7. The emitters must show wide doping window. In one embodiment, the emitter shows wide doping window from 2 wt. %-30 wt. % (the device efficiency and CIE coordinates of the device are within the ranges described above).

8. The efficiency roll-off of the device fabricated must be low. In one embodiment, the efficiency roll-off of the device fabricated from the emitter in current invention is less than 10% at 1,000 $cd/m^2$.

9. The device must have high brightness in low operation voltage. In one embodiment, the devices show brightness greater than or equal to 40,000 $cd/m^2$ at 10 V.

Since the emitters in the current invention do not carry net charge and are soluble in common solvents, various device fabrication methods can be used in OLED fabrication. The emitters of the invention can be formed into thin films by vacuum deposition, spin-coating, inkjet printing or other known fabrication methods. Different multilayer OLEDs have been fabricated using the compounds of the present invention as light-emitting material or as dopant in the emitting layer. In general, the OLEDs are comprised on an anode and a cathode, between which are the hole transporting layer, light-emitting layer, and electron transporting or injection layer. The present invention makes use of an additional carrier confinement layer to improve the performance of the devices.

In one embodiment, the OLED is fabricated by vacuum deposition.

In another embodiment, the OLED is fabricated by solution process including spin coating and printing.

Examples

Following are examples that illustrate embodiments for practicing the invention.

These examples should not be construed as limiting. All percentages are by weight and all solvent mixture proportions are by volume unless otherwise noted.

Example 1—Synthesis of Intermediate 3102

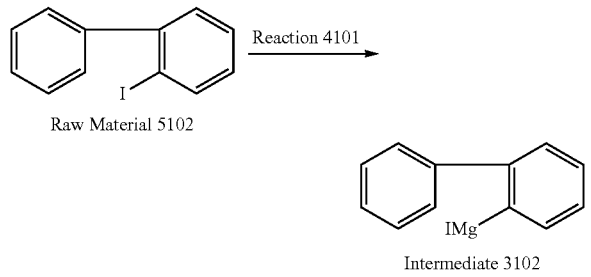

Raw Material 5102

Intermediate 3102

To a solution of magnesium (3.3 g, 137 mmol, 1.2 equiv.) and 40 mL of anhydrous diethyl ether was slowly added Raw Material 511 (41.5 mL, 137 mmol, 1.2 equiv.) via dropping funnel under nitrogen atmosphere. Intermediate 3101 was formed after stirring at reflux for 3 hours and used without further purification.

Example 2—Synthesis of Intermediate 3202

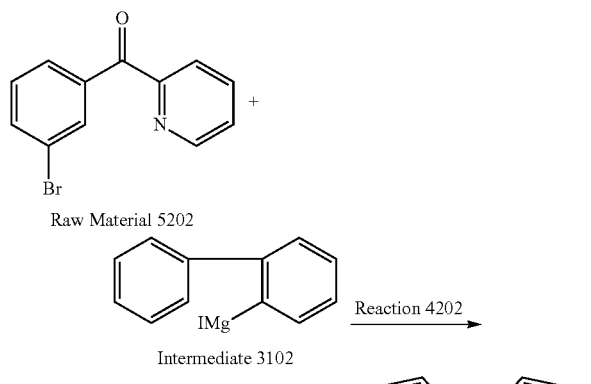

Raw Material 5202

Intermediate 3102

Intermediate 3202

To a solution of Raw Material 5202 (30.0 g, 114 mmol, 1.0 equiv.) in anhydrous THF (30 mL) was slowly added the Intermediate 3102 at room temperature under nitrogen atmosphere. After complete addition, the reaction mixture was stirred at reflux for 12 hours. The mixture was poured into a solution containing 5 mL concentrated $H_2SO_4$, 5 mL acetic anhydride and 90 mL acetic acid. The reaction mixture was stirred at 150° C. for 6 hours. The mixture was poured into methanol. After filtration and washing with cool methanol twice, the Intermediate 3202 was obtained as pale brown solid (29.0 g, 65%). $^1$H NMR (400 MHz, $CDCl_3$): δ7.36 (t, J=7.9 Hz, 1H), 7.50 (dd, J=7.6 Hz, J=4.8 Hz, 1H), 7.70 (d, J=8.0 Hz, 1H), 7.90 (dt, J=8.0 Hz, J=8.0 Hz, 1H) 8.04 (q, J=8.8 Hz, J=7.9 Hz, 2H), 8.22 (t, J=1.8 Hz, 1H), 8.72 (d, J=5.1 Hz, 1H).

Example 3—Synthesis of Intermediate 3302

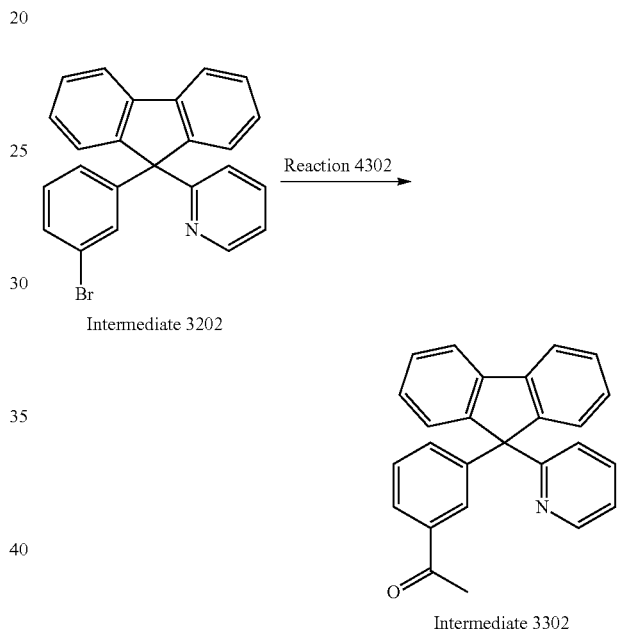

Intermediate 3202

Intermediate 3302

Stille coupling was employed for synthesizing Intermediate 3302. To a solution of Intermediate 3302 (29.0 g, 72.8 mmol, 1.0 equiv.), bis(triphenylphosphine)palladium(II) dichloride (5.1 g, 7.2 mmol, 10 mol %), and 80 mL anhydrous toluene was added 1-ethoxyvinyl tributylstannane (39.3 mL, 101.9 mmol, 1.4 equiv.) under nitrogen atmosphere. The reaction mixture was refluxed for 24 hours. After cooling, HCl (100 mL, 12M) was poured into the mixture, and extracted with dichloromethane (3×50 mL). The combined organic layers were washed with $H_2O$ (3×100 mL) and dried over $MgSO_4$. The solvent was removed under reduced pressure and the crude compound was purified by column chromatography on $SiO_2$ using ethyl acetate/hexane mixture (1:9) as eluent to afford Intermediate 3302 as light yellow solid (17.1 g, 66%). $^1$H NMR (300 MHz, $CDCl_3$): δ2.55 (s, 3H), 7.00 (d, J=7.9 Hz, 1H), 7.13 (t, J=5.2, 1H), 7.48-7.21 (m, 8H), 7.56 (d, J=7.6 Hz, 2H), 7.70 (s, 1H), 7.78 (t, J=7.4 Hz, 3H), 8.59 (d, J=4.1 Hz, 1H).

Example 4—Synthesis of Intermediate 3402

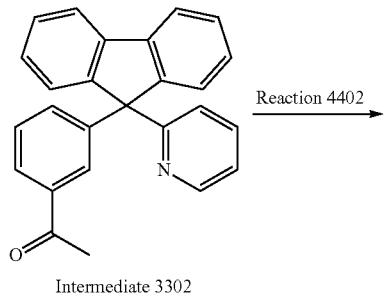

Intermediate 3302

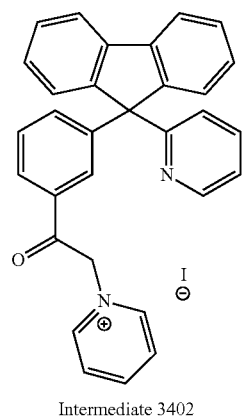

Intermediate 3402

A reaction mixture containing Intermediate 3302 (16.8 g, 46.4 mmol, 1 equiv.), iodine (17.7 g, 69.6 mmol, 1.5 equiv.) and pyridine (30 mL) was stirred at 150° C. for 2 hours. The mixture was concentrated under reduced pressure and washed with water twice. The Intermediate 3402 was allowed to re-crystallize in water/methanol mixture and obtained as pale brown solid (13.4 g, 51%). $^1$H NMR (400 MHz, CDCl$_3$): δ6.30 (s, 2H), 7.03 (d, J=8.0 Hz, 1H), 7.37-7.29 (m, 3H), 7.47-7.42 (m, 3H), 7.56 (t, J=7.8 Hz, 4H), 7.68 (t, J=7.8 Hz, 1H), 7.99-7.93 (m, 3H), 8.21 (t, J=6.7 Hz, 2H), 8.60 (d, J=4.6 Hz, 1H), 8.68 (t, J=7.8 Hz, 1H), 8.87 (d, J=5.8 Hz, 2H).

Example 5—Synthesis of Intermediate 3502

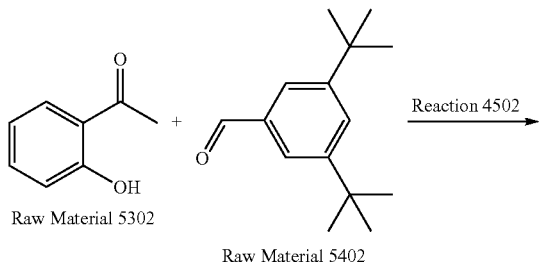

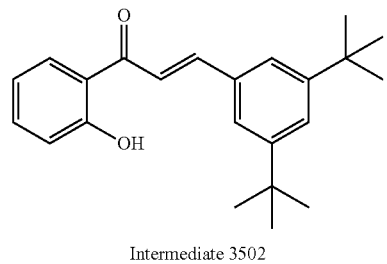

Intermediate 3502

To a solution of Raw Material 5402 (9.1 g, 41.5 mmol, 1 equiv.), Raw Material 5302 (5 mL, 41.5 mmol, 1 eq) and 30 mL ethanol was added NaOH (2.5 equiv., 10M). The resultant mixture was stirred at room temperature for 48 hours. After neutralization by acetic acid, the crude product was filtered and washed with cool ethanol (3×20 mL) to afford Intermediate 3502 as yellow solid (10.2 g, 73%). $^1$H NMR (400 MHz, CDCl$_3$): δ1.38 (s, 18H), 6.97 (s, 1H), 7.04 (s, 1H), 7.54-7.50 (m, 4H), 7.63 (d, J=15.5 Hz, 1H), 7.99-7.94 (m, 2H), 12.87 (s, 1H).

Example 6—Synthesis of Ligand 2002

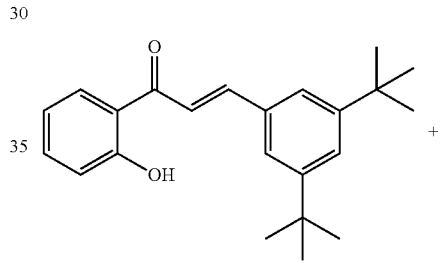

Intermediate 3502

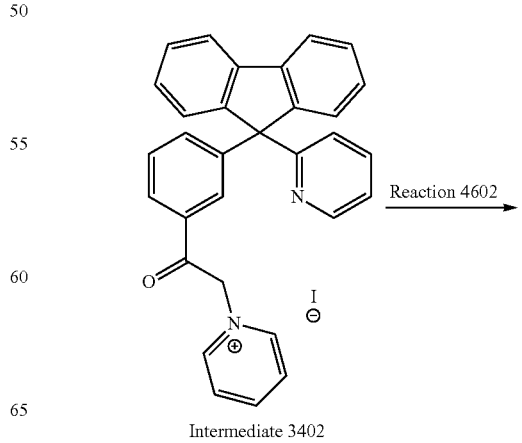

Intermediate 3402

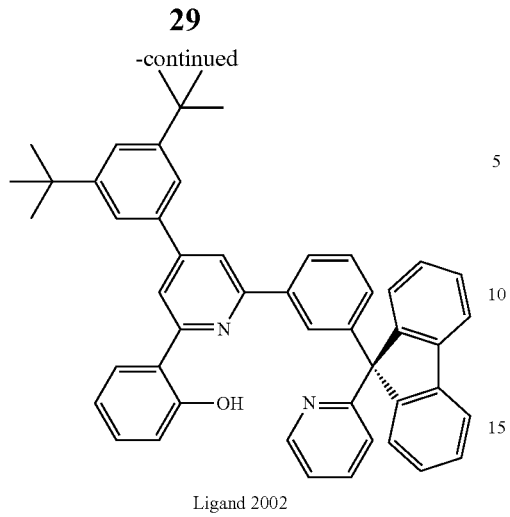

Ligand 2002

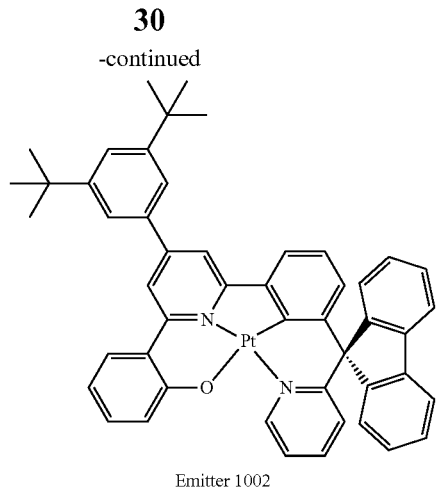

Emitter 1002

The reaction mixture containing Intermediate 3502 (10.4 g, 30.8 mmol, 1.2 equiv.), Intermediate 3402 (14.6 g, 25.7 mmol, 1.0 equiv.), ammonium acetate (19.8 g, 257 mmol, 10 equiv.) and glacial acetic acid (100 mL) was refluxed at 175° C. for 24 hours. The crude mixture was extracted with dichloromethane (3×60 mL). The combined organic phases were washed with H$_2$O (3×50 mL) and dried over MgSO$_4$. The solvent was removed under reduced pressure and the crude compound was purified by column chromatography on SiO$_2$ using ethyl acetate/hexane mixture (1:10) as eluent to afford Ligand 2002 as light yellow solid (4 g, 23%). $^1$H NMR (600 MHz, CDCl$_3$): δ1.40 (s, 18H, —CH$_3$), 6.92 (t, J=7.6 Hz, 1H, H$^5$), 7.04 (d, J=7.4 Hz, 1H, H$^3$), 7.08 (d, J=8.0 Hz, 1H, H$^{15}$), 7.13 (t, J=5.6 Hz, 1H, H$^{21}$), 7.17 (d, J=8.0 Hz, 1H, H$^{20}$), 7.32 (t, J=7.0 Hz, 3H, H$^4$, H$^{27}$), 7.39 (q, J=11.3 Hz, J=7.9 Hz, 3H, H$^{16}$, H$^{23}$, H$^{25}$), 7.44 (s, 2H, H$^{31}$), 7.48, (t, J=7.8 Hz, 1H, H$^{22}$), 7.56 (s, 2H, H$^{10}$, H$^{33}$), 7.73 (d, J=7.6 Hz, 3H, H$^{26}$, H$^{13}$), 7.80 (d, J=7.6 Hz, 2H, H$^{25}$), 7.88 (q, J=8.1 Hz, J=7.1 Hz, 2H, H$^6$, H$^{17}$), 7.96 (s, 1H, H$^8$), 8.70 (s, 1H, H$^{23}$), 14.63 (s, 1H, —OH).

Example 7—Synthesis of Emitter 1002

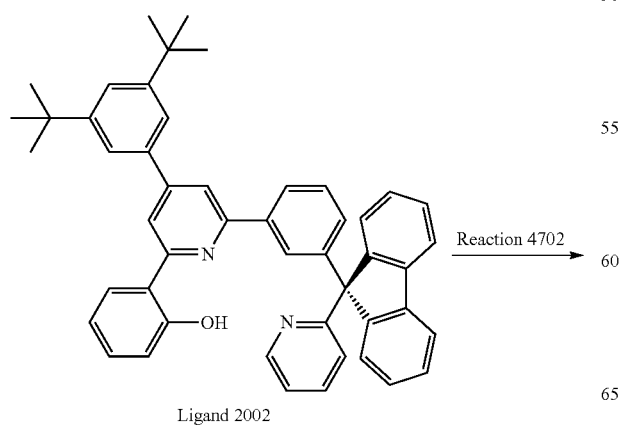

Ligand 2002

Reaction 4702

A mixture of K$_2$PtCl$_4$ (2.9 g, 7.0 mmol, 1.3 equiv.) and the Ligand 2002 (3.7 g, 5.4 mmol, 1.0 equiv.) in chloroform (5 mL) and glacial acetic acid (50 mL) was refluxed for 24 hours. The crude mixture was neutralized by sodium bicarbonate solution and extracted with dichloromethane (3×50 mL). The combined organic layers were washed with H$_2$O (3×50 mL) and dried over MgSO$_4$. The solvent was removed under reduced pressure and the crude product was purified by column chromatography on SiO$_2$ using ethyl acetate/hexane mixture (2:8) as eluent to afford Emitter 1002 as light yellow solid (1.5 g, 31%). $^1$H NMR (600 MHz, CDCl$_3$): δ1.43 (s, 18H, —CH$_3$), 6.36 (d, J=7.9 Hz, 1H, H$^{15}$), 6.78 (t, J=6.9 Hz, 1H, H$^5$), 6.85 (t, J=7.7 Hz, 1H, H$^{16}$), 6.92 (d, J=8.3 Hz, 1H, H$^{20}$), 7.28-7.30 (m, 3H, H$^3$, H$^{26}$), 7.38-7.45 (m, 4H, H$^4$, H$^{22}$, H$^{27}$), 7.60-7.64 (m, 3H, H$^{17}$, H$^{21}$, H$^{33}$), 7.65 (s, 2H, H$^{31}$), 7.84 (d, J=7.6 Hz, 2H, H$^{28}$), 7.89 (s, 1H, H$^{10}$), 8.02 (d, J=7.5 Hz, 1H, H$^6$), 8.09 (d, J=7.7 Hz, 2H, H$^{25}$), 8.21 (s, 1H, H$^8$), 10.40 (s, 1H, H$^{23}$). $^{13}$C NMR (150 MHz, CDCl$_3$) δ165.13, 164.54, 160.97, 153.30, 152.00, 151.79, 150.74, 150.44, 145.50, 140.64, 139.96, 139.01, 137.97, 137.88, 131.42, 130.38, 128.50, 128.20, 126.62, 126.27, 125.05, 123.84, 123.80, 123.48, 122.95, 122.80, 122.69, 121.45, 120.47, 118.80, 114.84, 113.52. MS (FAB): 867.29[M$^+$]. Anal. Calcd for C$_{49}$H$_{42}$N$_2$OPt: C, 67.65, H, 4.87, N, 3.22. Found: C, 67.07, H, 4.99, N, 3.06.

Example 8—Synthesis of Intermediate 3108

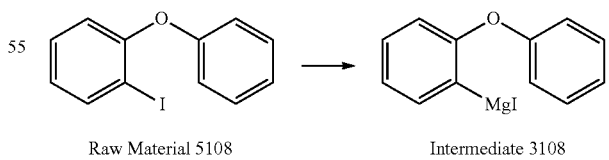

Raw Material 5108     Intermediate 3108

To a solution of magnesium (3.3 g, 137 mmol, 1.2 equiv.) and 40 mL of anhydrous diethyl ether was slowly added Raw Material 5108 (40.5 g, 137 mmol, 1.2 equiv.) via dropping funnel under nitrogen atmosphere. The Grignard reagent was formed after stirring at reflux for overnight and used without purification.

Example 9—Synthesis of Intermediate 3208

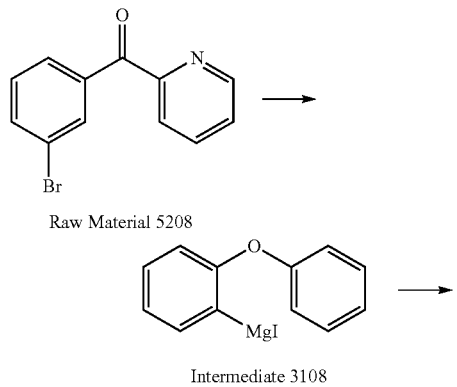

Raw Material 5208

Intermediate 3108

Intermediate 3208

To a solution of Raw Material 5208 (30.0 g, 114 mmol, 1.0 equiv.) in anhydrous THF (30 mL) was slowly added Intermediate 3108 at room temperature under nitrogen atmosphere. After complete addition, the reaction mixture was stirred at reflux for addition of 12 hours. The mixture was poured into a solution containing 5 mL concentrated $H_2SO_4$, 5 mL acetic anhydride and 90 mL acetic acid. The reaction mixture was stirred at 150° C. for 12 hours. The mixture was extracted with dichloromethane and combined organic layer was washed with $H_2O$ and dried over anhydrous $MgSO_4$. The product was purified by column chromatography using Hexane:Ethyl Acetate (8:2) as eluent. The compound was obtained as pale white solid (35.6 g, 63%). $^1$H NMR (400 MHz, $CDCl_3$): δ6.79 (d, J=8.0 Hz, 1H), 6.96-7.03 (m, 6H), 7.07 (t, J=7.9 Hz, 1H), 7.13 (d, J=8.1 Hz, 2H) 7.18-7.22 (m, 3H), 7.31 (d, J=7.2 Hz, 1H), 7.42 (t, J=5.86 Hz, 1H), 8.56 (d, J=4.7 Hz, 1H).

Example 10—Synthesis of Intermediate 3308

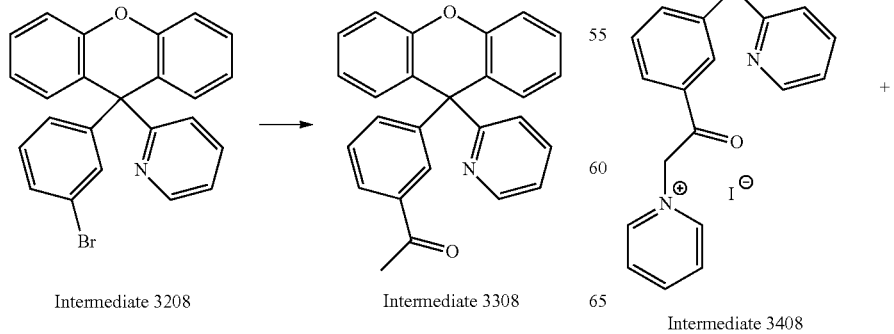

Intermediate 3208

Intermediate 3308

To a solution of Intermediate 3208 (35.6 g, 86.3 mmol, 1.0 equiv.), bis(triphenylphosphine)palladium(II) dichloride (6.1 g, 8.6 mmol, 10 mol %), and 80 mL anhydrous toluene was added 1-ethoxyvinyl tributylstannane (39.3 mL, 101.9 mmol, 1.2 equiv.) under nitrogen atmosphere. The reaction mixture was refluxed for 48 hours. After cooling, HCl (100 mL, 12M) was poured into the mixture, and extracted with dichloromethane (3×50 mL). The combined organic layers were washed with $H_2O$ (3×100 mL) and dried over $MgSO_4$. The solvent was removed under reduced pressure and the crude compound was purified by column chromatography on $SiO_2$ using ethyl acetate/hexane mixture (1:9) as eluent to afford Intermediate 3308 as light yellow solid (19.5 g, 65%). $^1$H NMR (400 MHz, $CDCl_3$): δ 2.45 (s, 3H), 6.83 (d, J=7.6 Hz, 1H), 6.97-7.01 (m, 4H), 7.12 (t, J=7.6 Hz, 1H), 7.15 (d, J=8.0 Hz, 2H), 7.23-7.28 (m, 3H), 7.34 (t, J=7.8 Hz, 1H), 7.67 (s, 1H), 7.8 (d, J=4.8 Hz, 1H) 8.6 (d, J=4.1 Hz, 1H).

Example 11—Synthesis of Intermediate 3408

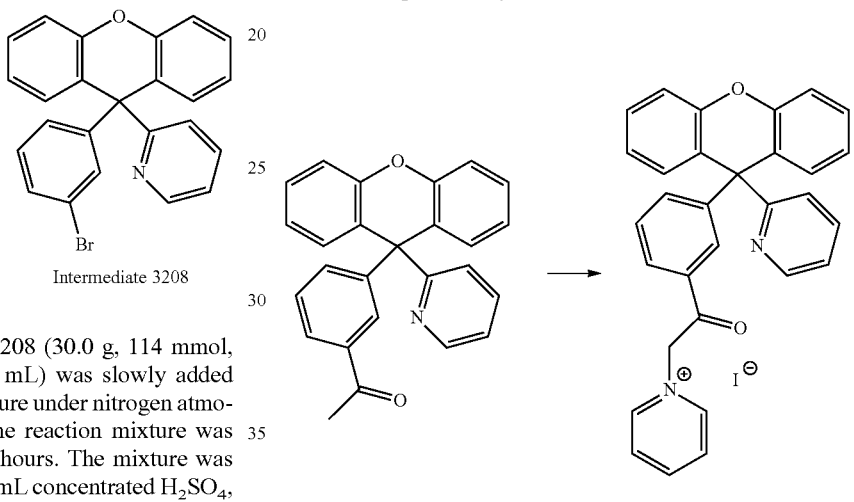

Intermediate 3308

Intermediate 3408

A reaction mixture containing Intermediate 3380 (19.5 g, 51.8 mmol, 1 equiv.), iodine (17.7 g, 69.6 mmol, 1.3 equiv.) and pyridine (30 mL) was stirred at 150° C. for 8 hours. The mixture was concentrated under reduced pressure. Intermediate 3408 was used for the next step without purification.

Example 12—Synthesis of Ligand 2008

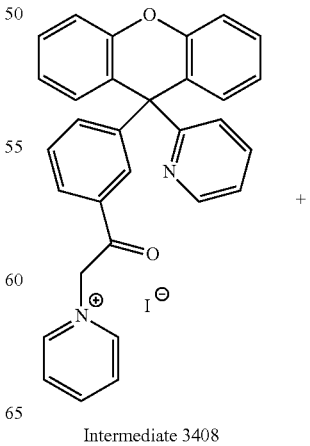

Intermediate 3408

+

-continued

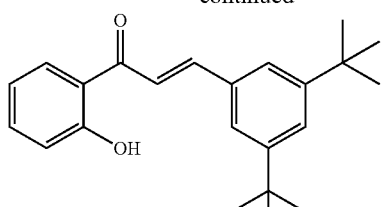

Intermediate 3502

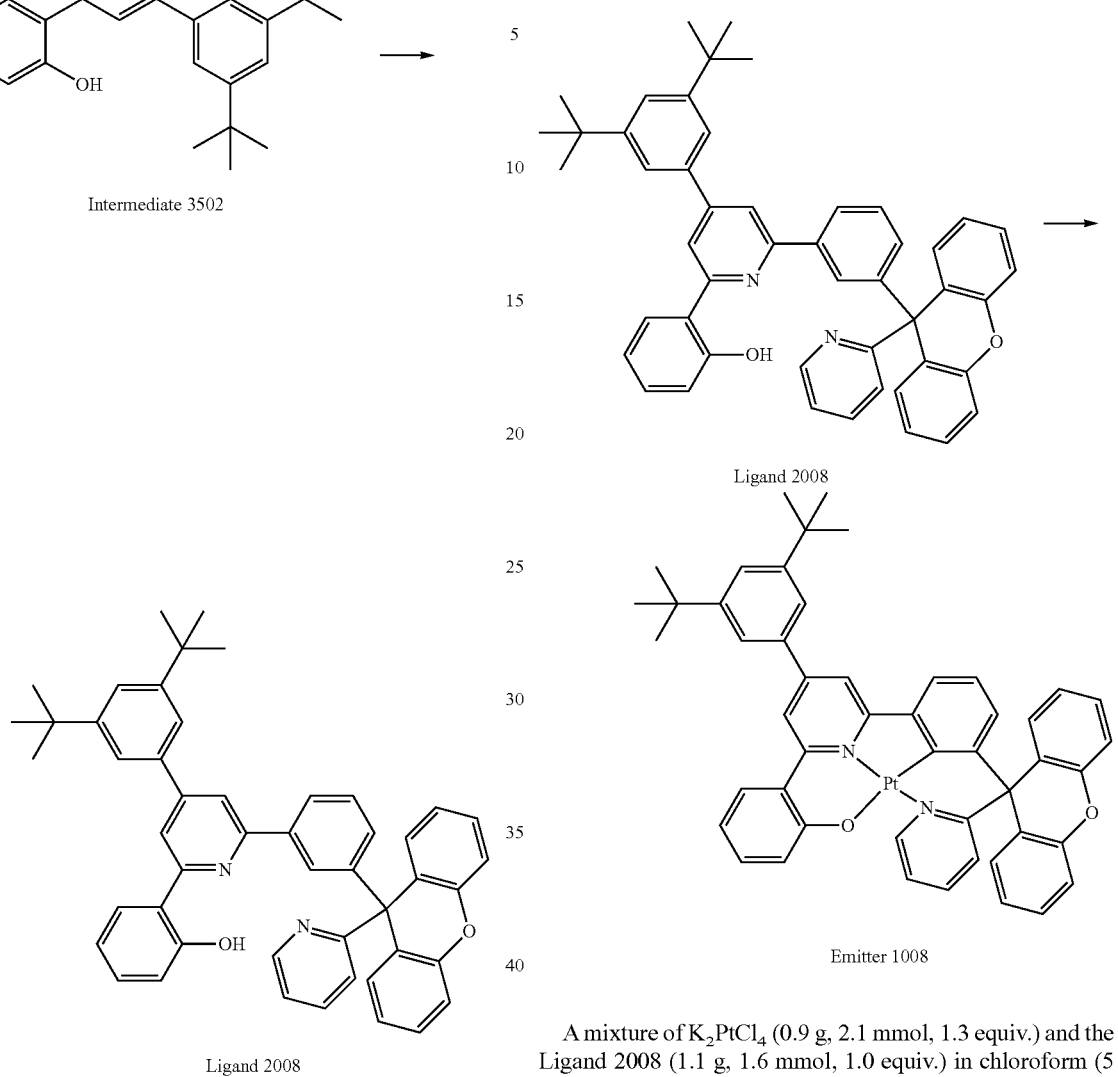

Ligand 2008

The reaction mixture containing Intermediate 3502 (1.4 g, 4.1 mmol, 1.2 equiv.), Intermediate 3408 (2 g, 3.4 mmol, 1.0 equiv.), ammonium acetate (2.6 g, 34.0 mmol, 10 equiv.) and glacial acetic acid (100 mL) was refluxed at 175° C. for 24 hours. The crude mixture was extracted with dichloromethane (3×60 mL). The combined organic phases were washed with H$_2$O (3×50 mL) and dried over MgSO$_4$. The crude product was purified by column chromatography on SiO$_2$ using ethyl acetate/hexane mixture (1:10) as eluent to afford Ligand 2008 as yellow solid (1.1 g, 47%). $^1$H NMR (300 MHz, CDCl$_3$): δ 1.31 (s, 18H, —CH$_3$), 6.85-7.01 (m, 7H), 7.03-7.09 (m, 4H), 7.17-7.23 (m, 4H), 7.35-7.40 (m, 3H), 7.48-7.54 (m, 3H), 7.60 (s, 1H), 7.83 (q, J=6.8 Hz, J=8.0 Hz, 2H), 7.94 (s, 1H), 8.53 (d, J=3.9 Hz, 1H) 14.21 (s, 1H, —OH).

Example 13—Synthesis of Emitter 1008

A mixture of K$_2$PtCl$_4$ (0.9 g, 2.1 mmol, 1.3 equiv.) and the Ligand 2008 (1.1 g, 1.6 mmol, 1.0 equiv.) in chloroform (5 mL) and glacial acetic acid (50 mL) was refluxed for 24 hours. The solvent was removed under reduced pressure and the crude product was purified by column chromatography on SiO$_2$ using ethyl acetate/hexane mixture (2:8) as eluent to afford Emitter 1008 as light yellow solid (0.38 g, 38%). $^1$H NMR (600 MHz, CD$_2$Cl$_2$): δ 0.66-0.82 (m, 10H), 1.08-1.17 (m, 4H), 2.02-2.10 (m, 4H), 6.70-6.73 (m, 2H), 6.81-6.85 (m, 2H), 6.96 (t, J=7.6 Hz, 1H), 7.16-7.32 (m, 8H), 7.51 (t, J=7.5 Hz, 2H), 7.56 (d, J=7.7 Hz, 1H), 7.67 (t, J=6.7 Hz, 1H), 7.83 (d, J=7.7 Hz, 1h), 10.73 (s, 1H).

Example 14—X-Ray Diffraction Data of Emitter 1002

The structure is depicted in FIG. 2 which shows the emitter is not in planar structure. X-Ray diffraction data of single crystals were collected on a MAR PSD diffractometer with a 300 mm image plate detector or Bruker X8 Proteum diffractometer. The diffraction images were interpreted and diffraction intensities were integrated using program DENZO and the crystal structures were solved by direct methods employing SHELXS-97 program.

| Formula | $C_{49}H_{42}N_2OPt$ |
|---|---|
| Temperature, K | 100 |
| Formula weight | 869.29 |
| Crystal system | triclinic |
| Space group | P-1 |
| a, Å | 12.4607(5) |
| b, Å | 12.7920(5) |
| c, Å | 14.1587(6) |
| α, deg | 67.97(1) |
| β, deg | 85.66(1) |
| γ, deg | 68.67(1) |
| Cell volume, Å$^3$ | 1944.0(14) |
| Z | 1 |
| Density, calculated, g/cm$^3$ | 1.588 |
| mm$^{-1}$ | 8.013 |
| Index ranges | h = −14→13 |
| | k = −15→15 |
| | i = −16→15 |
| F(000) | 930 |
| Theta range, deg | 3.4-66.1 |
| $R_1$ | 0.0439 |
| $wR_2$ | 0.1182 |
| GoF | 1.097 |
| largest diff. peak/hole [e Å$^{-3}$] | 2.46/−1.42 |

Note: $R_1 = \Sigma ||F_o| - |F_c||/\Sigma|F_o|$, $wR_2 = \{\Sigma[w(F_o^2 - F_c^2)^2]/\Sigma[w(F_o^2)^2]\}^{1/2}$ Example 15—Physical Data for Emitter 1002

The UV-Vis absorption and emission spectra of Emitter 1002 is depicted in FIG. 3.

| UV-Vis absorption[a] | Emission[a] | | | | |
|---|---|---|---|---|---|
| $\lambda_{max}$ [nm] (ε [mol$^{-1}$dm$^3$cm$^{-1}$]) | $\lambda_{max}$ [nm] (τ [μs]) | $\Phi_{em}$[b] | $k_q$[c] [mol$^{-1}$dm$^3$s$^{-1}$] | HOMO [eV][d] | LUMO [eV][d] |
| 261 (49763), 279 (54453), 301 (36052), 329 (17799), 356 (17400), 393 (7227), 431 (3826) | 517 (5.10), 535 (5.10) | 0.80 | 1.1 × 10$^7$ | −5.3 | −2.6 |

[a]Determined in degassed CH$_2$Cl$_2$ (2 × 10$^{-5}$ mol dm$^{-3}$).
[b]Emission quantum yield was esitmated with BPEA (9,10-bis(phenylethynyl)anthracene) in degassed CH$_3$CN as standard ($\Phi_{em}$ = 0.85).
[c]Self-quenching constant.
[d]The HOMO and LUMO levels were estimated from onset potentials in cyclic voltammery study using Cp$_2$Fe$^{0/+}$ value of 4.8 eV below the vacuum level.

Example 15—Key Performance of OLEDs Fabricated from Emitter 1002

All OLEDs were constructed with a simple architecture of ITO/MoO$_3$ (5 nm)/HTL (50 nm)/TCTA:Emitter 1002 (10 nm)/ETL (50 nm)/LiF (1.2 nm)/Al (150 nm). TAPC (di-[4-(N,N-ditolyl-amino)-phenyl]cyclohexane) was used as the hole-transporting layer (HTL) while TmPyPB (1,3,5-tri(m-pyrid-3-yl-phenyl)) or Tm3PyBPZ (2,4,6-tris(3-(3-(pyridin-3-yl)phenyl)phenyl)-1,3,5-triazine) as the electron-transporting layer (ETL).

| C[a] | L[b] (cd m$^{-2}$) | $V_{on}$[d] (V) | Max. PE[e] (lm/W) | EQE[f] (%) Max. | EQE[f] (%) at 1000 cd m$^{-2}$ | EQE[f] (%) at 10000 cd m$^{-2}$ | CIE[g] (x, y) |
|---|---|---|---|---|---|---|---|
| 2 wt %[h] | 19000 | 2.9 | 99.6 | 24.9 | 20.4 | 9.59 | (0.29, 0.64) |
| 6 wt %[h] | 40000 | 2.8 | 106.7 | 26.9 | 26.2 | 19.1 | (0.31, 0.64) |
| 10 wt %[h] | 47000 | 2.7 | 109.4 | 27.6 | 25.6 | 20.0 | (0.31, 0.64) |
| 30 wt %[h] | 49700 | 2.7 | 95.7 | 24.0 | 21.9 | 17.9 | (0.33, 0.63) |
| 10 wt %[i] | 35300 | 2.4 | 126 | 26.4 | 23.4 | 13.6 | (0.31, 0.63) |

[a]doping concentration;
[b]luminance at 12 V;
c) luminance at 10 V;
[d]turn-on voltage: the driving voltage at luminance ~1 cd m$^{-2}$;
[e]Power efficiency;
[f]external quantum efficiency;
[g]CIE coordinates at 1000 cd m$^{-2}$;
[h]TmPyPb is used as the electron-transporting layer.
[i]Tm3PyBPZ is used as the electron-transporting layer.

The graphs are depicted in FIG. 4-FIG. 8.

Example 16—Theory Calculation and Femtosecond Time-Resolved Fluorescent Measurements To account for the high efficiency and low efficiency roll-off of Emitter 1002 OLEDs, theory calculations and femtosecond time-resolved fluorescence measurements have been performed. TDDFT calculations at M062X/6-311G*(lanl2dz) level based on the geometries of triplet excited states of Emitter 1002 give emission wavelength of 512 nm, which is in agreement with the experimental data (517 nm). As expected, for Emitter 1002, the geometrical differences between T$_1$ and S$_0$ states are very small, which means very slow non-radiative decay rate constants (k$_{nr}$) of T$_1$ to S$_0$. The optimized geometries of Emitter 1002 dimmers are shown in FIG. 9. The calculated geometrical parameters are in good agreement with the X-ray crystallography data. The Pt—Pt distances is 4.616 Å, no Pt—Pt interactions arise.

The HOMO and LUMO are mainly localized on the O^N^C^N ligand (see FIG. 10). The emission is mainly from HOMO-1→LUMO+1 (81.4%), which is mainly attributed to the π-π* transition of the substituent of the ligand.

Femtosecond time-resolved fluorescence measurement with CH$_2$Cl$_2$ solution of Emitter 1002 ($\lambda_{ex}$=350 nm) revealed fluorescence (FIG. 11) that decays with time constant of ~0.15 ps. This extremely rapid decay of fluorescence is suggestive of the presence of nearly unitary efficiency nonradiative decay attributed to efficient ISC from the electronically excited singlet to give the triplet states.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. An organic light-emitting diode (OLED) emitter having a chemical structure of Structure I:

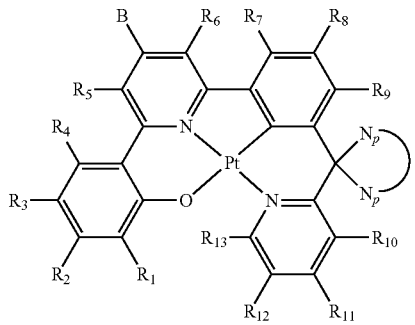

wherein $R_1$-$R_{13}$ are independently selected from a first group consisting of: hydrogen, halogen, an unsubstituted alkyl, a substituted alkyl, cycloalkyl, an unsubstituted aryl, and a substituted aryl;
each pair of adjacent R groups of $R_1$-$R_{13}$ can independently join together to form a 5-8 member ring;
B is a hydrocarbon group containing 4 to 24 carbon atoms; and

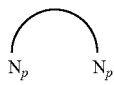

is a group having a chemical structure of Structure II:

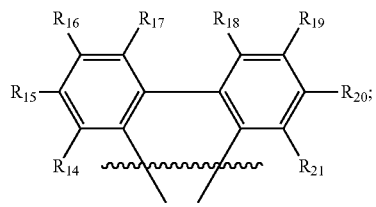

wherein $R_{14}$-$R_{21}$ are independently selected from a second group consisting of: another hydrogen, another halogen, a hydroxy, another unsubstituted alkyl, another substituted alkyl, another cycloalkyl, another unsubstituted aryl, another substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, and an alkoxycarbonyl group; and
each pair of adjacent R groups of $R_{14}$-$R_{21}$ can independently join together to form a 5-8 member ring.

2. The OLED emitter in claim 1, wherein in the first group the unsubstituted alkyl contains 1 to 10 carbon atoms, the substituted alkyl contains 1 to 20 carbon atoms, the cycloalkyl contains 4 to 20 carbon atoms, the unsubstituted aryl contains 6-20 carbon atoms, and the substituted aryl contains 6 to 20 carbon atoms.

3. The OLED emitter in claim 1, wherein B is:

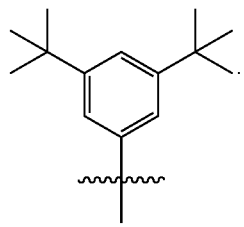 [SMILES: *c1cc(C(C)(C)C)cc(C(C)(C)C)c1]

4. The OLED emitter in claim 1, wherein in the second group the another unsubstituted alkyl contains from 1 to 10 carbon atoms, the another substituted alkyl contains from 1 to 20 carbon atoms, the another cycloalkyl contains from 4 to 20 carbon atoms, the another unsubstituted aryl contains from 6 to 20 carbon atoms, the another substituted aryl contains from 6 to 20 carbon atoms, the acyl contains from 1 to 20 carbon atoms, the alkoxy contains from 1 to 20 carbon atoms, the acyloxy contains from 1 to 20 carbon atoms, the acylamino contains from 1 to 20 carbon atoms, the aralkyl contains from 7 to 20 carbon atoms, the carboxyl contains from 1 to 20 carbon atoms, the aminocarbonyl contains from 1 to 20 carbon atoms, the carbamoyl contains from 1 to 20 carbon atoms, the aryloxycarbonyl contains from 7 to 20 carbon atoms, the phenoxycarbonyl contains from 7 to 20 carbon atoms, and the alkoxycarbonyl group contains from 2 to 20 carbon atoms.

5. The OLED emitter in claim 1, wherein the emitter is selected from:

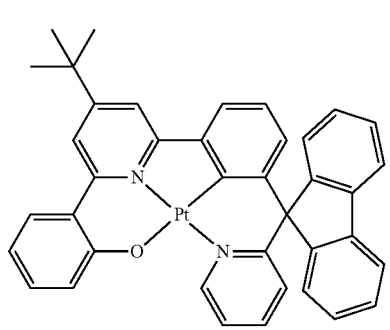

Emitter 101

Emitter 102
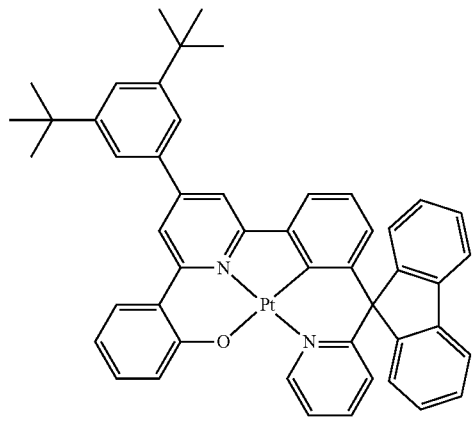
Emitter 103
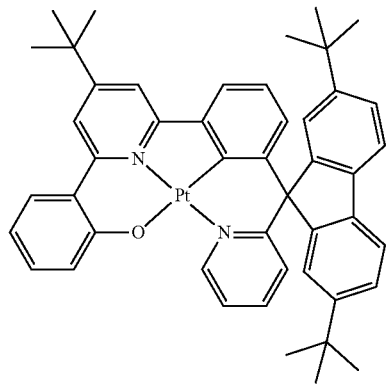
Emitter 104
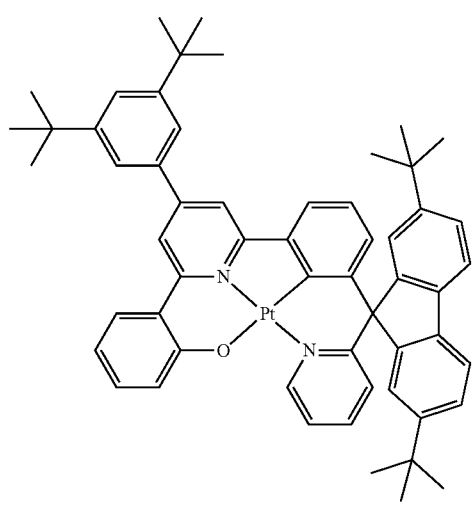
Emitter 109
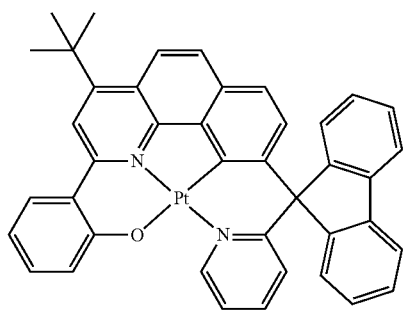
Emitter 110
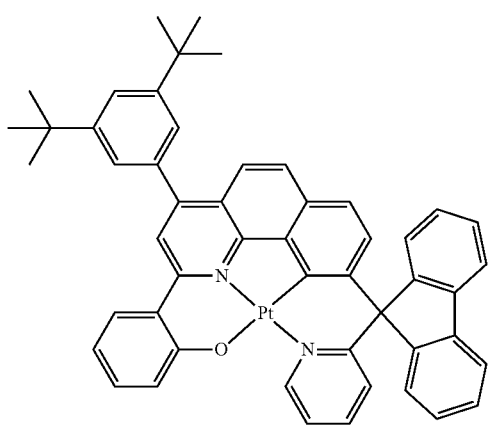
Emitter 111
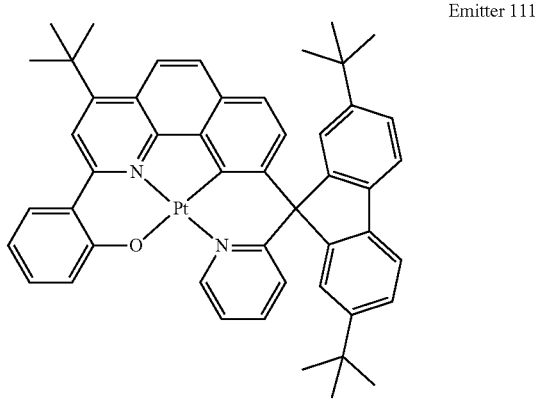
Emitter 112
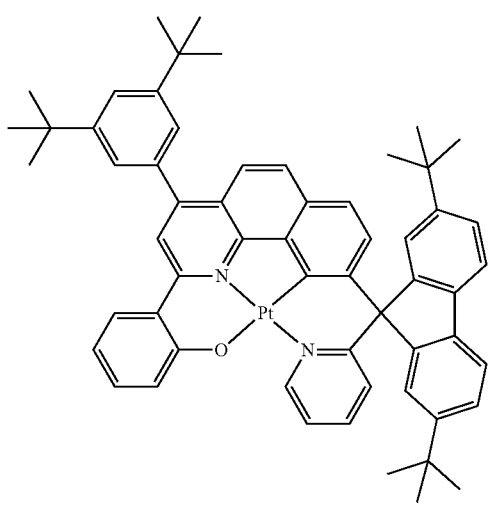

Emitter 117
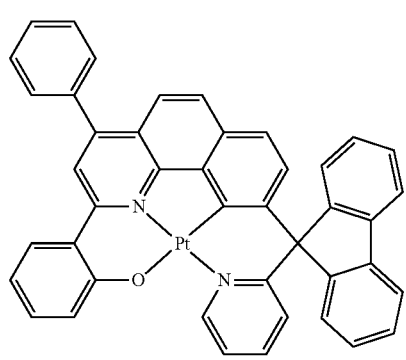
Emitter 118
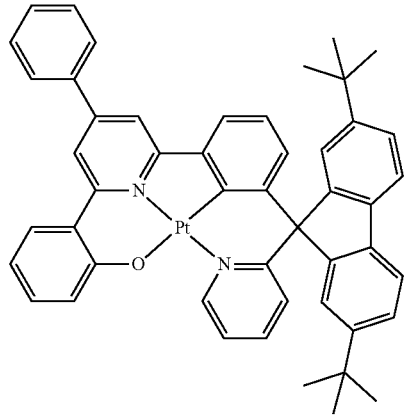
Emitter 119
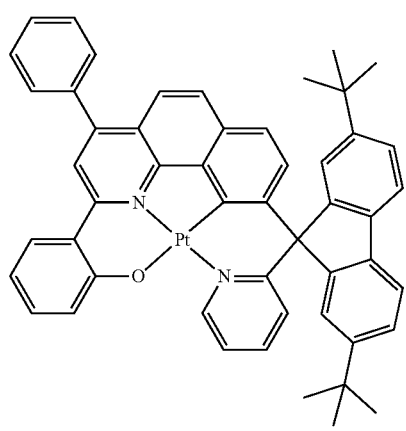
Emitter 120
Emitter 123
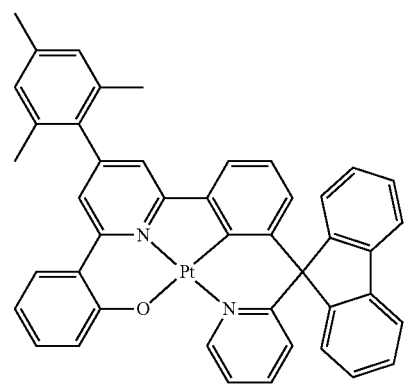
Emitter 124
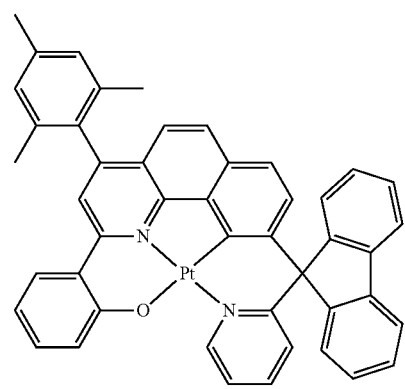
Emitter 125
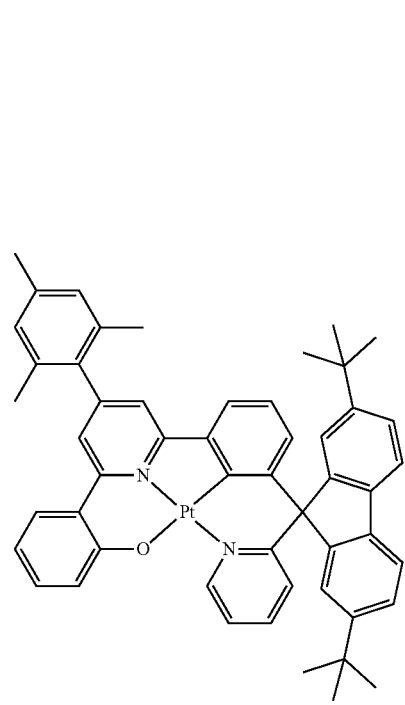

-continued

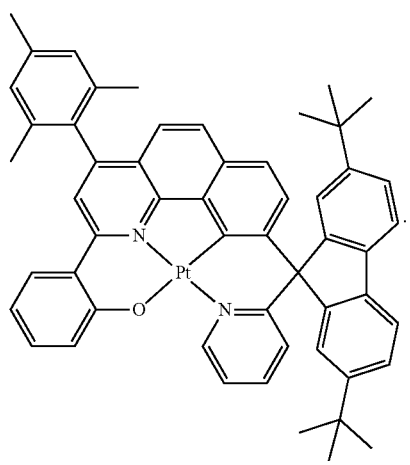

Emitter 126

6. The OLED emitter in claim 1 having a green emission in solution and an emission $\lambda_{max}$<520 nm.

7. The OLED emitter in claim 1 having a short emission lifetime of less than 6 μs.

8. The OLED emitter in claim 1 having a self-quenching constant equal to or less than $10^7$ $dm^3$ $mol^{-1}$ $s^{-1}$.

9. A light-emitting device comprising at least one OLED emitter of claim 1 as an emitting material.

10. The light-emitting device of claim 9, wherein the device is an organic light-emitting diode (OLED).

11. The light-emitting device of claim 9, wherein the device is fabricated by vacuum deposition.

12. The light-emitting device of claim 9, wherein the device is fabricated by solution processes.

13. The light-emitting device of claim 9, wherein the device contains one emissive layer.

14. The light-emitting device of claim 9, wherein the device contains more than one emissive layer.

15. The light-emitting device of claim 9, wherein the efficiency roll-off at 1000 cd/m² is less than 10%.

16. The light-emitting device of claim 9, wherein the doping concentration of the emitter is from 2-30 weight %;
   a change in an x chromaticity coordinate of a Commission Internationale de l'Elcairage (CIE) color model is less than 0.04 between the doping concentrations of the emitter; and
   a change in a y chromaticity coordinate of the CIE color model is less than 0.02 between the doping concentrations of the emitter.

17. An organic light-emitting diode (OLED) emitter having a chemical structure of Structure I:

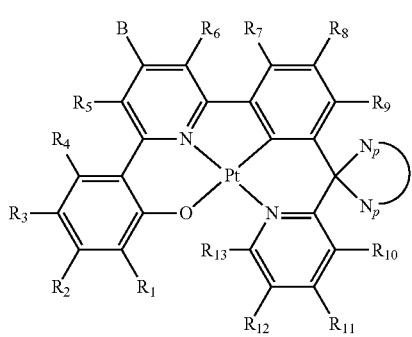

wherein $R_1$-$R_{13}$ are independently selected from a first group consisting of: hydrogen, halogen, an unsubstituted alkyl, a substituted alkyl, cycloalkyl, an unsubstituted aryl, and a substituted aryl;

each pair of adjacent R groups of $R_1$-$R_{13}$ can independently join together to form a 5-8 member ring;

B is a hydrocarbon group containing 4 to 24 carbon atoms; and

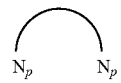

is a group having a chemical structure of Structure II:

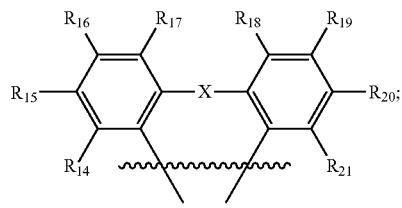

wherein $R_{14}$-$R_{21}$ are independently selected from a second group consisting of: another hydrogen, another halogen, a hydroxy, another unsubstituted alkyl, another substituted alkyl, another cycloalkyl, another unsubstituted aryl, another substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, and an alkoxycarbonyl group;

X is selected from a fourth group consisting of: oxygen and sulfur; and wherein each pair of adjacent R groups of $R_{14}$-$R_{21}$ can independently join together to form a 5-8 member ring.

18. The OLED emitter in claim 17, wherein the emitter is selected from:

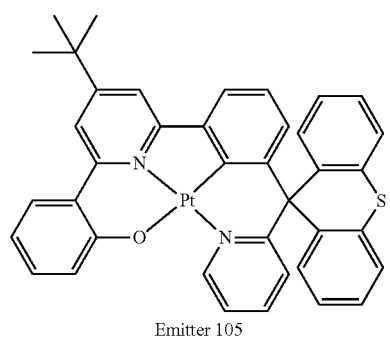

Emitter 105

-continued
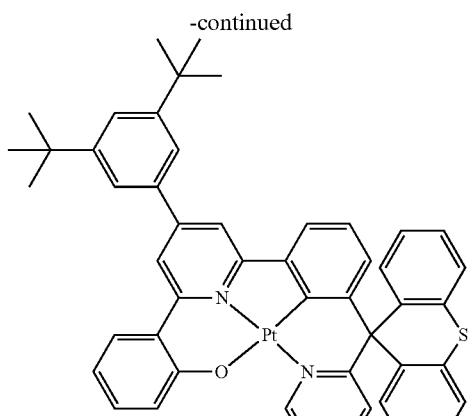
Emitter 106
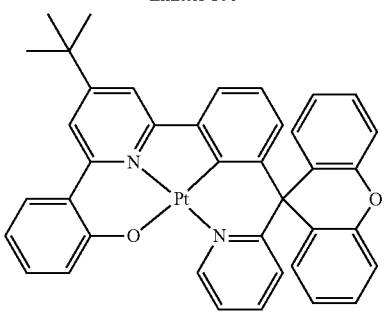
Emitter 107
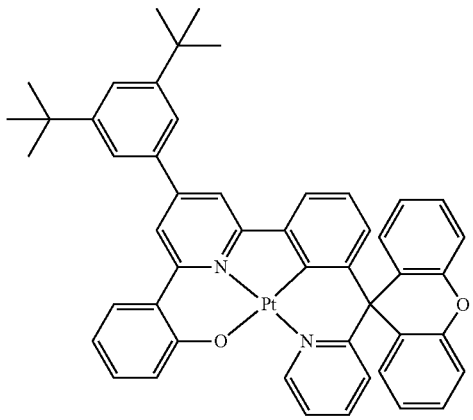
Emitter 108
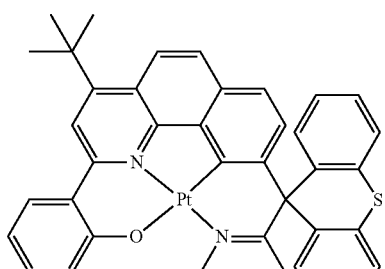
Emitter 113
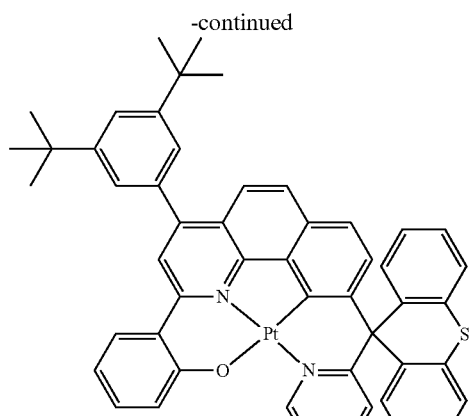
Emitter 114
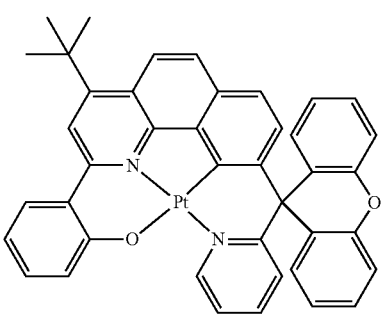
Emitter 115
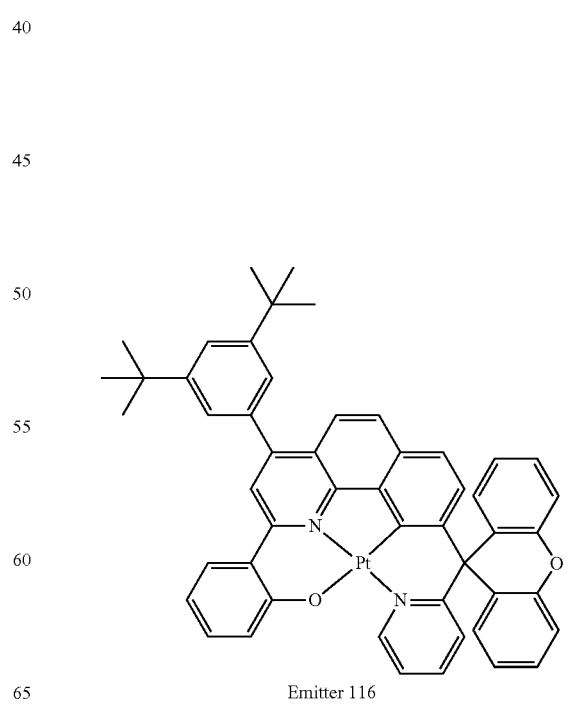
Emitter 116

-continued
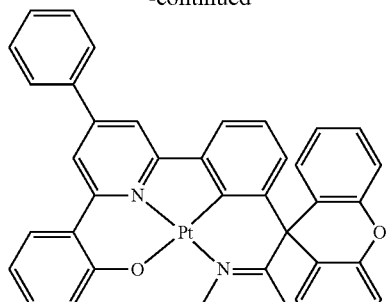
Emitter 121
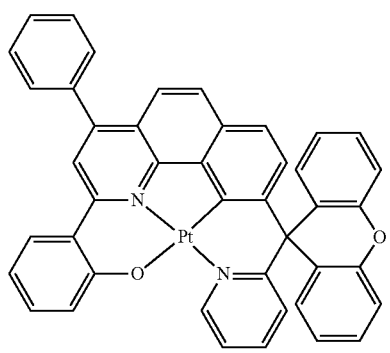
Emitter 122
-continued
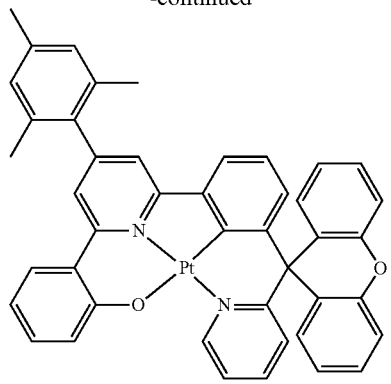
Emitter 127
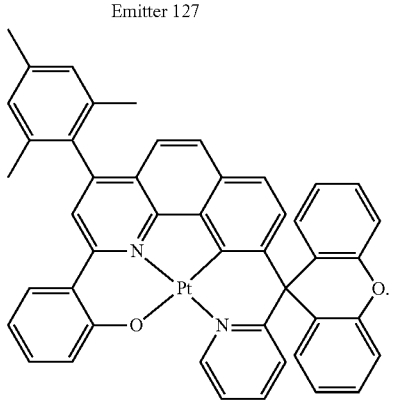
Emitter 128
* * * * *